United States Patent [19]

Sueda et al.

[11] Patent Number: 5,576,335
[45] Date of Patent: Nov. 19, 1996

[54] UREA DERIVATIVES AND THEIR USE AS ACAT INHIBITORS

[75] Inventors: Noriyoshi Sueda, Ohimachi; Kazuhiko Yamada, Komoro; Makoto Yanai, Ohimachi; Katsutoshi Miura, Ohimachi; Masato Horigome, Ohimachi; Norio Oshida, Ohimachi; Shigeru Hiramoto, Ohimachi; Koichi Katasuyama, Ohimachi; Fumihisa Nakata, Ohimachi; Nobuhiro Kinoshita, Ohimachi; Yoko Tsukada, Ohimachi, all of Japan

[73] Assignee: Nisshin Flour Milling Co., Ltd., Saitama-ken, Japan

[21] Appl. No.: 314,814

[22] Filed: Sep. 29, 1994

[30] Foreign Application Priority Data

Feb. 1, 1994 [JP] Japan .................................. 6-027560

[51] Int. Cl.⁶ ..................... C07D 211/26; C07D 213/36; A61K 31/445; A61K 31/44
[52] U.S. Cl. ..................... 514/317; 544/224; 544/349; 544/382; 544/390; 546/332; 546/285; 546/306; 514/357; 514/597; 514/598; 514/249; 514/255; 514/353; 564/50; 564/51; 564/52
[58] Field of Search ..................... 564/50, 51; 514/597, 514/317, 598; 544/224; 546/332

[56] References Cited

U.S. PATENT DOCUMENTS

| | | | |
|---|---|---|---|
| 3,660,486 | 5/1972 | Thiele et al. | 260/553 A |
| 5,116,848 | 5/1992 | Trivedi | 514/332 |
| 5,214,206 | 5/1993 | Picard et al. | 564/40 |
| 5,258,405 | 11/1993 | Ito et al. | 514/597 |

FOREIGN PATENT DOCUMENTS

| | | | |
|---|---|---|---|
| 0450660 | 10/1991 | European Pat. Off. | C07C 275/30 |
| 0477778 | 4/1992 | European Pat. Off. | |
| 3822448A1 | 3/1990 | Germany | C07C 275/40 |

OTHER PUBLICATIONS

Morel, D., et al, "Endothelial and Smooth Muscles . . . ", Arteriosclerosis, 4, 357–364 (1984) Month of publication not provided.

Kita, T., et al, "Probucol prevents the progression . . . ", Proc. Natl. Acad. Sci., USA 84, 5928–5931 (1987) Month of publication not provided.

Largis, E. E., et al, J. Lipid Research 30, 681–690 (1989), "CL 277,082: a novel inhibitor . . . " Month of publication not provided.

Natori, K., et al, "Mechanism of the Inhibition of Cholesterol . . . "Japan J. Pharm., 42, 517–523 (1986) Month of publication not provided.

Mao, S. J. T., et al, "Antioxidant Activity of Probucol . . . " J. Med. Chem., 34, 298–302 (1991) Month of publication not provided.

Kornev, K. A. et al. *Chemical Abstract Service*, Abstract No. 70:67779 (1968).

Shibasaki et al. *Chemical Abstract Service*, Abstract No. 69:86908 (1968).

Swinyard, E. A. et al. *Remington's Pharmaceutical Sciences*, ed. Gennaro, A. R. et al. (Mack Pub. Co., Easton) pp. 1286–1304 (1990).

*Primary Examiner*—Cecilia Tsang
*Assistant Examiner*—King Lit Wong
*Attorney, Agent, or Firm*—Michael N. Meller

[57] ABSTRACT

Urea derivatives of formula (1)

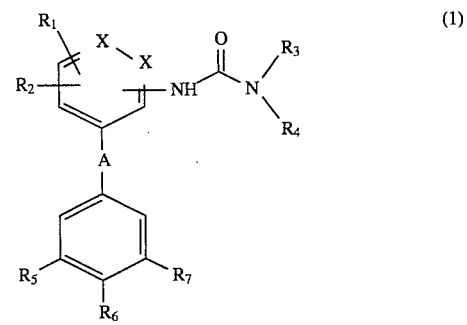

wherein the valuable groups are as defined in the specification, which possess both an ACAT inhibitory activity and an antioxidative activity. Those derivatives are useful in the prophylaxis and treatment of hypercholesterolemia and atherosclerosis.

7 Claims, No Drawings

UREA DERIVATIVES AND THEIR USE AS ACAT INHIBITORS

FIELD OF THE INVENTION

This invention relates to new urea derivatives, processes for their preparation and their use in medicine. More particularly, the invention relates to compounds having an inhibitory activity against an acyl coenzyme A cholesterol acyltransferase (called hereafter ACAT) and having a protective ability against an oxidative modification of low density lipoprotein (called hereafter LDL).

BACKGROUND OF THE INVENTION

In recent years, an interest has been directed to the relationship between an increase in the level of cholesterol in the serum and a human health condition. It has been pointed out that the level of cholesterol in the serum is associated with the amount of cholesterol deposited in the blood vessel system and the deposition of cholesterol in the blood vessel system brings about e.g. lesion of coronary artery, which is responsible for ischemic heart disease.

Drugs for reducing the level of cholesterol in the serum have been developed. These drugs, however, were effective in controlling blood cholesterol to an appropriate level, but ineffective in inhibiting absorption of cholesterol from the digestive tracts and deposition of cholesterol on the wall of blood vessels.

ACAT is an enzyme that catalyzes the synthesis of cholesteryl esters from acyl coenzyme A and cholesterol and plays an important role in metabolism of cholesterol and its absorption from the digestive tracts. It is believed that ACAT occurs in the site of mucosa cells of the intestinal tracts and is active in esterification and incorporation of cholesterol derived from the diet. On the other hand, the cholesterol deposited on the wall of blood vessels is the esterified cholesterol. The cholesterol accumulated in the foam cells which plays an important role in the formation of atherosclerosis lesion is also esterified cholesterol. The enzyme that catalyzes the esterification of cholesterol in these sites is also ACAT.

Accordingly, the inhibition of an ACAT activity can result in inhibiting the incorporation in vivo of cholesterol derived from the diet and further the formation of cholesteryl ester in specified cell sites.

Compounds having an ACAT inhibitory activity are disclosed in EP 0450660 A1 and EP 0477778 A2. However, those known compounds have only an ACAT inhibitory activity and give no effect on the oxidative modification of LDL causing the foam cell transformation of macrophage which is an important phenomenon for the formation of atherosclerosis lesion.

The foam cells which play an important role in the formation of atherosclerosis lesion are a product of uptake of oxidatively modified LDL into macrophage which results in the foam cell transformation of the macrophage. It is reported by Diane W. Morel et al. (Arteriosclerosis, Vol. 4, pages 357–364, 1984) that, the oxidatively modified LDL causes foam cell transformation of macrophage and plays an important role in the formation of atherosclerosis lesion. A report of TORU KITA et al. (Proc. Natl. Acad. Sci. USA, Vol. 84, pages 5928–5931, 1987) demonstrates that prevention of the oxidative modification of LDL induces regression of the atherosclerosis lesion. Therefore, inhibition of the oxidative modification of LDL, in addition to the above-mentioned ACAT inhibitory activity, is very important in preventing the formation and progression as well as inducing regression of atherosclerosis lesion.

Under such circumstances, it has been desired to develop the compound having an ACAT inhibitory activity and being capable of inhibiting an oxidative modification of LDL or the like, since such a compound may decrease the serum cholesterol level and inhibit the oxidative modification of LDL cholesterol deposited on the blood vessel or tissue, thus being effective for inhibiting the formation and progression of atherosclerosis lesions and inducing its regression.

DETAILED DESCRIPTION OF THE INVENTION

We have now found new urea derivatives which exhibit both an ACAT inhibitory activity and an antioxidative activity. The urea derivatives of the present invention possess an ACAT inhibitory activity, thereby inhibiting an absorption of cholesterol from the intestinal tracts, lowering a blood cholesterol level and inhibiting an accumulation of cholesteryl esters in the wall of blood vessels, atheroma and macrophage, and simultaneously an antioxidative activity i.e. a protective activity against the oxidative modification of LDL which participates in foam cell transformation of macrophage thereby effectively inhibiting the formation and progression of atherosclerosis lesion and inducing its regression.

According to one aspect of the present invention, there is provided a compound of formula (1) and pharmaceutically acceptable salts thereof.

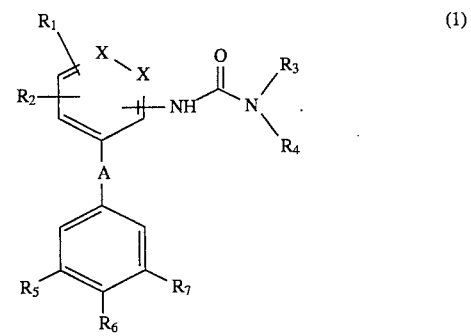

in which:

$R_1$ and $R_2$, which may be the same or different, each represents
 a hydrogen atom,
 a halogen atom,
 a $(C_1-C_6)$alkoxy group, $R_3$ and $R_4$, which may be the same or different, each represents
 a hydrogen atom,
 a $(C_1-C_8)$alkyl group,
 a cyclo$(C_3-C_8)$alkyl group,
 an aryl$(C_1-C_6)$alkyl group,
  in which the aryl moiety is optionally substituted by one or two substituents selected from the group consisting of halogen, $(C_1-C_6)$alkyl and $(C_1-C_6)$alkoxy,
 a diaryl$(C_1-C_6)$alkyl group,
 a pyridyl$(C_1-C_6)$alkyl group,
 a diazabicyclo$(C_7-C_{10})$alkyl group optionally substituted by $(C_1-C_6)$alkyl,
 an adamantyl group or
 a piperidyl group optionally substituted by aryl$(C_1-C_6)$alkyl, and further $R_3$ and $R_4$, together with the nitrogen atom to which they are attached, may form a 5 or 6 membered ring monocyclic, heterocyclic group optionally substituted by $(C_1-C_6)$alkyl, $R_5$ and $R_7$, which may be the same or different, each represents a hydrogen atom or a $(C_1-C_6)$alkyl group, $R_6$ represents —$OR_8$ or —$N(R_8)_2$ wherein $R_8$ represents a hydrogen atom or a $(C_1-C_6)$alkyl group, or —$C(O)NHR_3$ wherein $R_3$ is as defined above, $R_6$ and $R_7$ together may form —O—$CH_2$—O— which may be fused with a phenyl ring, X represents a nitrogen atom or a methine group, A represents

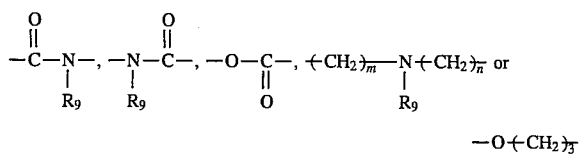

wherein $R_9$ represents a hydrogen atom, a $(C_1-C_6)$alkyl group, a $(C_1-C_6)$alkylcarbonyl group, a geranyl group or —$C(O)NHR_3$, and m and n independently represent 0, 1 or 2, the alkyl and alkoxy groups or moieties represented by $R_1$ to $R_9$ may be straight or branched.

Referring to $R_1$ and $R_2$ in formula (1), the halogen atom includes fluorine, chlorine, bromine and iodine, and the $(C_1-C_6)$alkoxy group includes e.g. methoxy, ethoxy, propoxy, isopropoxy, butoxy, isobutoxy, sec-butoxy, tert-butoxy, pentyloxy and hexyloxy.

Referring to $R_3$ and $R_4$ in formula (1), the $(C_1-C_8)$alkyl group includes e.g. methyl, ethyl, propyl, isopropyl, butyl, isobutyl, sec-butyl, tert-butyl, pentyl, isopentyl, tert-pentyl, neopentyl, hexyl, 2-methylpentyl, 2-ethylpentyl, 4-methylhexyl, heptyl and octyl. The cyclo$(C_3-C_8)$alkyl group includes e.g. cyclopropyl, cyclobutyl, cyclopentyl, cyclohexyl, cycloheptyl and cyclooctyl. The aryl$(C_1-C_6)$alkyl group includes e.g. benzyl, phenethyl, 3-phenylpropyl, 4-phenylbutyl, 5-phenylpentyl, 6-phenylhexyl, 3-phenylhexyl, 2-naphthylmethyl, 2-naphthylethyl, 2-methylbenzyl, 4-ethylbenzyl, 3-chlorobenzyl, 4-chlorobenzyl, 4-fluorobenzyl, 2,4-difluorobenzyl, 4-methoxybenzyl, 3,4-dimethoxybenzyl, 4-chlorophenethyl and 3,4-dimethoxyphenethyl. The diaryl$(C_1-C_6)$alkyl group includes e.g. diphenylmethyl, 2,2-diphenylethyl, 3,3-diphenylpropyl, 4,4-diphenylbutyl and 4,6-diphenylhexyl. The pyridyl$(C_1-C_6)$alkyl group includes e.g. 2-pyridylmethyl, 3-pyridylmethyl, 2-(2-pyridyl)ethyl, 2-(3-pyridyl)propyl and 4-(2-pyridyl)butyl. The diazabicyclo$(C_7-C_{10})$alkyl group includes e.g. 3,9-diazabicyclo[3.3.1]nonan-7-yl, 3,9-dimethyl-3,9-diazabicyclo[3.3.1]nonan-7-yl, 3-ethyl-9-methyl-3,9-diazabicyclo[3.3.1]nonan-7-yl and 3-methyl-9-propyl-3,9-diazabicyclo[3.3.1]nonan-7-yl. The piperidyl group optionally substituted by aryl$(C_1-C_6)$alkyl includes e.g. benzylpiperidyl, phenethylpiperidyl, 3-phenylpropylpiperidyl, 4-phenylbutylpiperidyl, 5-phenylpentylpiperidyl and 6-phenylhexylpiperidyl. When $R_3$ and $R_4$, together with the nitrogen atom to which they are attached, form the 5- or 6-membered, monocyclic, heterocyclic group optionally substituted by $(C_1-C_6)$alkyl group, said heterocyclic group includes e.g. pyrrolidinyl, pyrazolidinyl, imidazolidinyl, pyrrolyl, pyrazolyl, imidazolyl, piperidyl, piperazinyl, 2-methylpyrrolidinyl, 3-methylpyrazolidinyl, 2-methylimidazolidinyl, 3-methylpyrrolyl, 2-ethylpiperidyl and 4-ethylpiperazinyl.

The $(C_1-C_6)$alkyl group represented by $R_5$, $R_7$, $R_8$ and $R_9$ includes e.g. methyl, ethyl, propyl, isopropyl, butyl, isobutyl, sec-butyl, tert-butyl, pentyl, isopentyl, tert-pentyl, neopentyl, hexyl and 2-methylpentyl.

The $(C_1-C_6)$alkylcarbonyl group represented by $R_9$ includes e.g. acetyl, propionyl, butyryl, isobutyryl, valeryl, isovaleryl and pivaloyl.

It should be understood that the compounds of formula (1) include all of their possible isomers including stereoisomer, metabolite and metabolic precursor.

The compounds of formula (1) can be prepared by various conventional procedures, for example, the methods shown in Schemes 1, 2, 3, 4, 5 and 6 below.

The compounds of formula (1) wherein A represents —$C(O)N(R_9)$— ($R_9$ represents hydrogen, alkyl or geranyl) can be prepared by reacting a compound of formula (2a) ($R_1$, $R_2$ and X are as defined above) with a halogenation agent such as thionyl chloride, phosphorus trichloride, phosphorus pentachloride and oxalyl chloride to form a corresponding chloride of formula (2b), followed by reacting with a compound of formula (3) ($R_5$, $R_6$ and $R_7$ are as defined above and $R_9$ represents hydrogen, alkyl or geranyl) in an organic solvent in the presence of an acid binder to form a compound of formula (4); or alternatively reacting a compound of formula (2a) with a compound of formula (3) in an organic solvent in the presence of a condensation agent such as dicyclohexylcarbodiimide and 1-ethyl-3-(3-diethylaminopropyl)carbodiimide to form a compound of formula (4); reducing the compound of formula (4) with a reducing agent such as zinc, iron, tin and tin(II) chloride in an acid solution such as hydrochloric acid and acetic acid to form a compound of formula (5) or alternatively subjecting the compound of formula (4) to catalytic hydrogenation using a catalyst such as palladium/carbon and platinum oxide in an alcohol solvent such as methanol and ethanol to form a compound of formula (5); and reacting the compound of formula (5) with an isocyanate RNCO of formula (6) (R=$R_3$ or $R_4$, $R_3$ and $R_4$ are as defined above) in an organic solvent under ice-cooling or at a temperature up to room temperature.

The above reactions are shown in Scheme 1 below.

Scheme 1

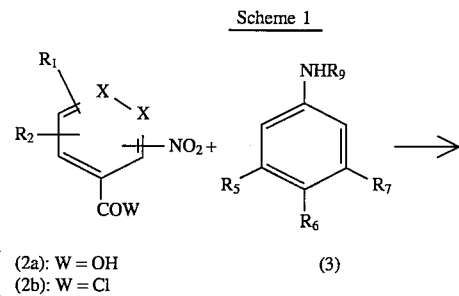

(2a): W = OH
(2b): W = Cl (3)

-continued
Scheme 1

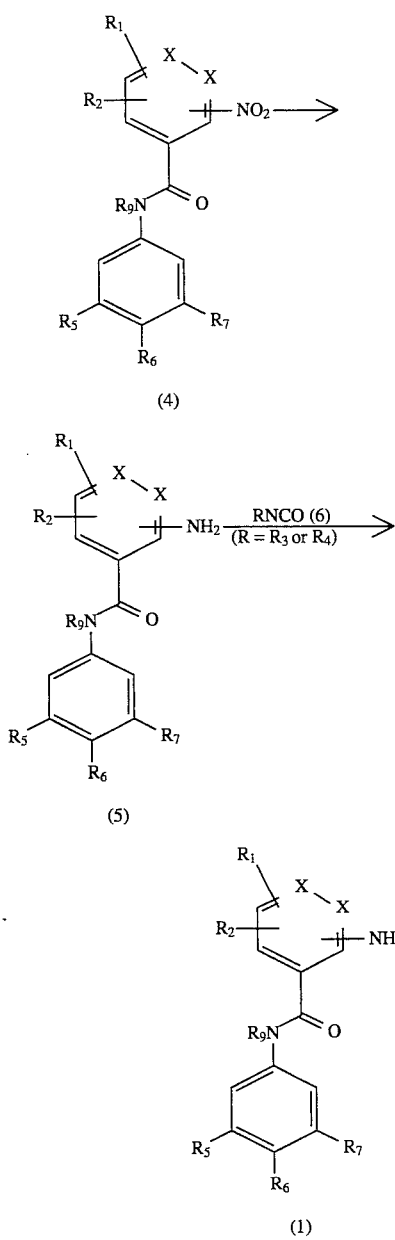

The compounds of formula (1) wherein A represents —N(R$_9$)C(O)— (R$_9$ represents hydrogen, alkyl or geranyl) or —OC(O)— can be prepared by reacting a compound of formula (8a) (R$_5$, R$_6$ and R$_7$ are as defined above) with a halogenation agent such as thionyl chloride, phosphorus trichloride, phosphorus pentachloride and oxalyl chloride to form a corresponding chloride of formula (8b), followed by reacting with a compound of formula (7) (R$_1$, R$_2$ and X are as defined above, Y represents NR$_9$ or OH, and R$_9$ represents hydrogen, alkyl or geranyl) in an organic solvent in the presence of an acid binder to form a compound of formula (9a) or (9b); or alternatively reacting a compound of formula (8a) with a halogenation agent such as thionyl chloride, phosphorus trichloride, phosphorus pentachloride and oxalyl chloride to form a corresponding chloride of formula (8b), followed by reacting with a compound of formula (10) (R$_1$, R$_2$, X and Y are as defined above) in an organic solvent in the presence of an acid binder or alternatively reacting a compound of formula (8a) with a compound of formula (10) in an organic solvent in the presence of a condensation agent such as dicyclohexylcarbodiimide and 1-ethyl-3-(3-diethylaminopropyl)carbodiimide to form a compound of formula (11a) or (11b); reducing the compound of formula (11a) or (11b) with a reducing agent such as zinc, iron, tin and tin(II) chloride in an acid solution such as hydrochloric acid and acetic acid to form a compound of formula (9a) or (9b) or alternatively subjecting the compound of formula (11a) or (11b) to catalytic hydrogenation using a catalyst such as palladium/carbon and platinum oxide in an alcohol solvent such as methanol and ethanol to form a compound of formula (9a) or (9b); and reacting the compound of formula (9a) or (9b) with an isocyanate RNCO of formula (6) in an organic solvent under ice-cooling or at a temperature up to room temperature.

Alternatively, the compounds of formula (1) can be prepared by reacting a compound of formula (9a) or (9b) with phenyl chloroformate in an organic solvent under ice-cooling or at a temperature up to room temperature in the presence of an acid binder to form a compound of formula (12a) or (12b) and reacting the compound of formula (12a) or (12b) with a compound of formula (13) (R$_3$ and R$_4$ are as defined above) in an organic solvent at a temperature of 50° to 150° C.

The above reactions are shown in Scheme 2 below.

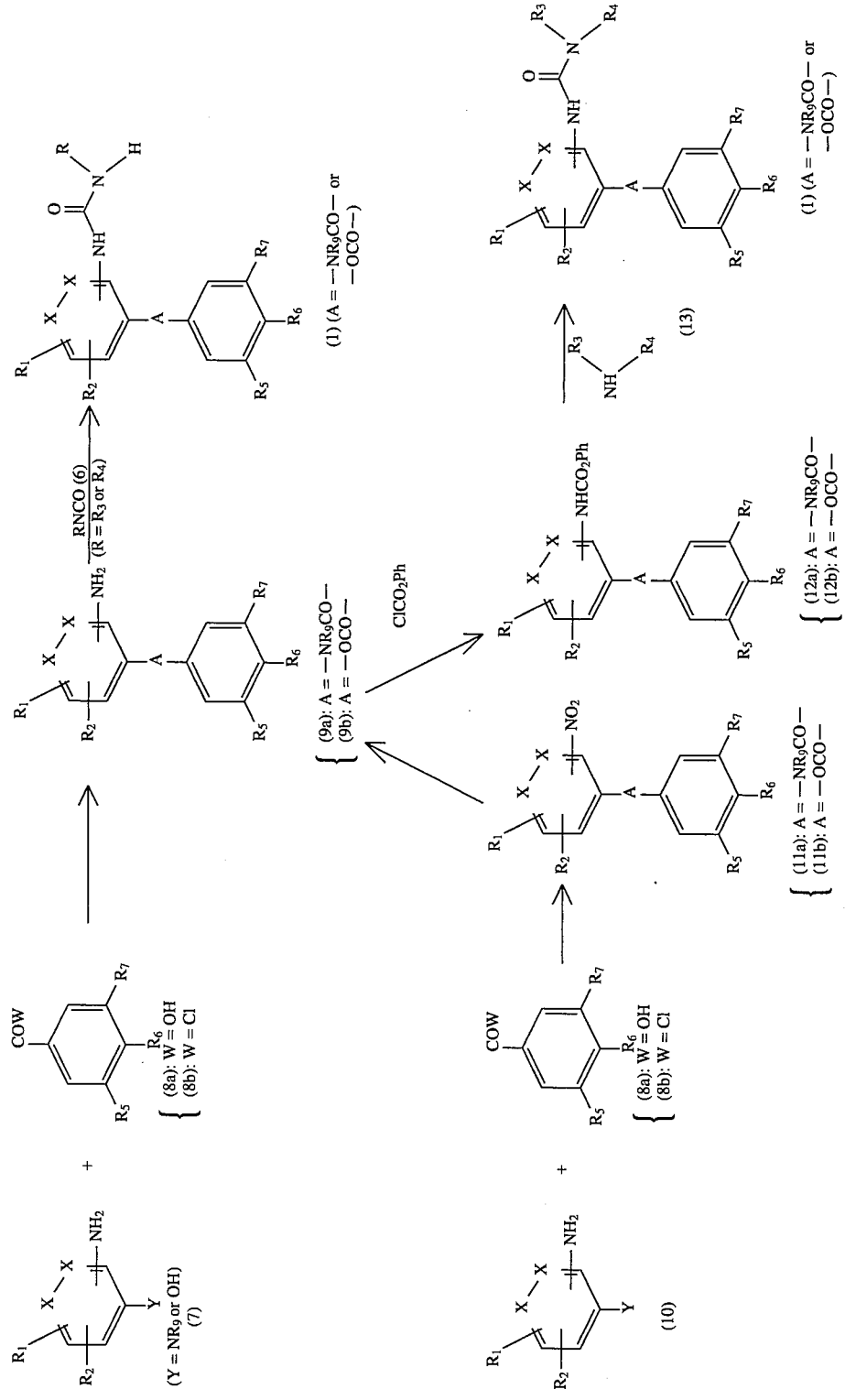

Alternatively, the compounds of formula (1) are prepared by the following procedures.

A compound of formula (14) ($R_1$, $R_2$ and X are as defined above and Z represents $NH_2$, OH or $NO_2$) is reacted with an isocyanate of formula (6) in an organic solvent under ice-cooling or at a temperature up to room temperature to form a compound of formula (15a). Alternatively, a compound of formula (14) is reacted with phenyl chloroformate in an organic solvent under ice-cooling or at a temperature and oxalyl chloride. Alternatively, the compounds of formula (1) are prepared by reacting a compound of formula (8a) with a compound of formula (15a) or (15b) in an organic solvent in the presence of a condensation agent such as dicyclohexylcarbodiimide and 1-ethyl-3-(3diethylaminopropyl)carbodiimide.

The above reactions are shown in Scheme 3 below.

Scheme 3

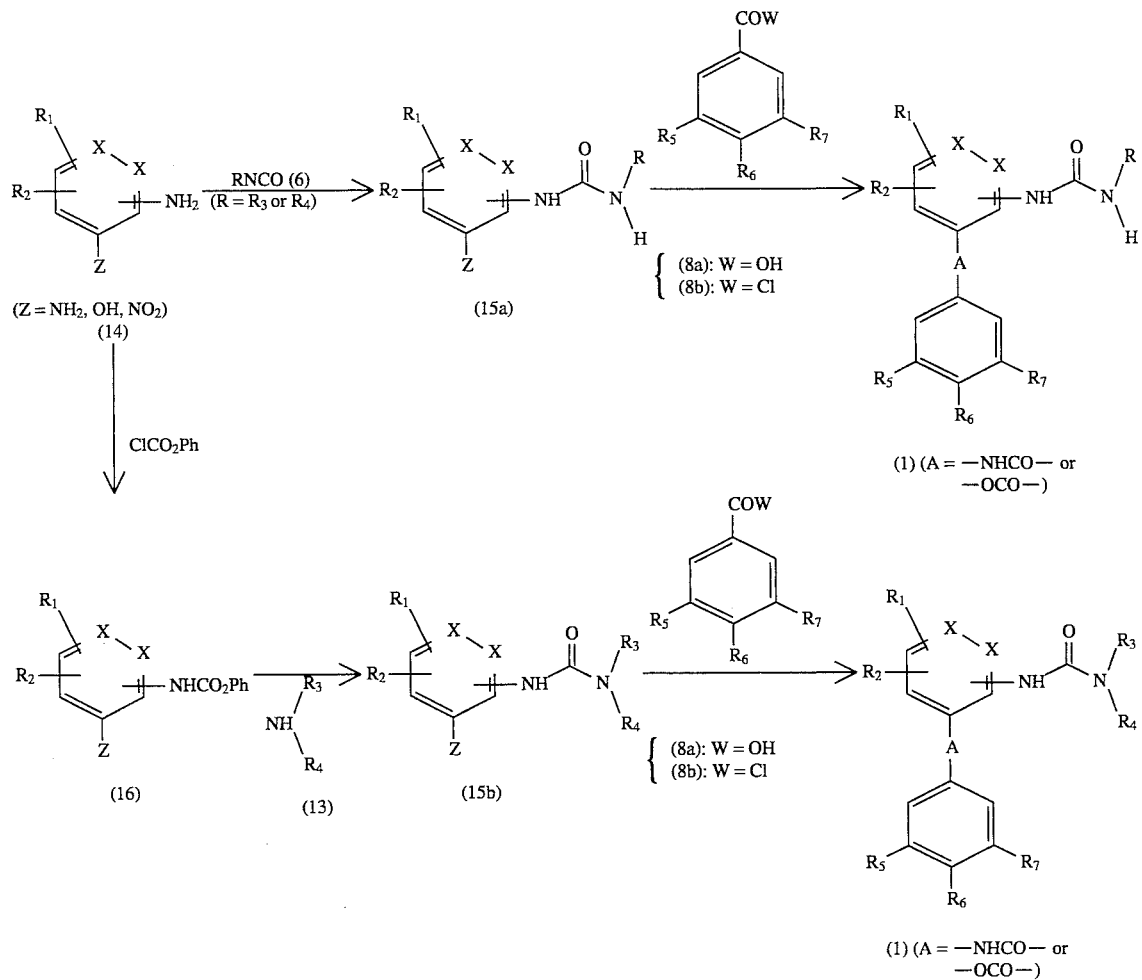

up to room temperature in the presence of an acid binder to form a compound of formula (16), followed by reaction with a compound of formula (13) to give a compound of formula (15b). The compound of formula (15a) or (15b) wherein Z is $NO_2$ is reduced with a reducing agent such as zinc, iron, tin and stannic chloride in an acid solution such as hydrochloric acid and acetic acid or alternatively subjected to catalytic hydrogenation using a catalyst such as palladium/carbon and platinum oxide in an alcohol solvent such as methanol and ethanol to form a compound of formula (15a) or (15b) wherein Z is $NH_2$. Subsequently, the compound of formula (15a) or (15b) is reacted with a compound of formula (8b) in an organic solvent in the presence of an acid binder to afford the compounds of formula (1). The compound of formula (8b) is prepared by reacting a compound of formula (8a) with a halogenation agent such as thionyl chloride, phosphorus trichloride, phosphorus pentachloride The compounds of formula (1) wherein A represents —$(CH_2)_m N(R_9)(CH_2)_n$— ($R_9$ represents hydrogen, alkyl, alkylcarbonyl geranyl or —$CONHR_3$ ($R_3$ is as defined above)) can be prepared by reacting a compound of formula (17) ($R_1$, $R_2$, m and X are as defined above and Q represents halogen, p-toluenesulfonyl or methanesulfonyl) with a compound of formula (18) ($R_5$, $R_6$, $R_7$, $R_9$, and n are as defined above) at a temperature between room temperature and a reflux temperature in an organic solvent in the presence of an acid binder to give a compound of formula (19); reducing the compound of formula (19) with a reducing agent such as zinc, iron, tin and tin(II) chloride in an acid solution such as hydrochloric acid and acetic acid or alternatively subjecting the compound of formula (19) to catalytic hydrogenation using a catalyst such as palladium/carbon and platinum oxide in an alcohol solvent such as methanol and ethanol to give a compound of formula (20); and reacting the compound of formula (20) with an isocyanate RNCO of formula (6) in an organic solvent under ice-cooling or at a temperature up to room temperature.

The compound of formula (1) wherein $R_9$ is hydrogen is reacted with an isocyanate of formula (6) in an organic solvent under ice-cooling or at a temperature up to room temperature to form a compound of formula (1) wherein $R_9$ is $CONHR_3$ ($R_3$ is as defined above).

The compound of formula (1) wherein $R_9$ is hydrogen is reacted with an acid chloride or an acid anhydride in an organic solvent in the presence of an acid binder under ice-cooling or at a temperature up to room temperature to form a compound of formula (1) wherein $R_9$ is alkylcarbonyl group.

The above reactions are shown in Scheme 4 below.

Scheme 4

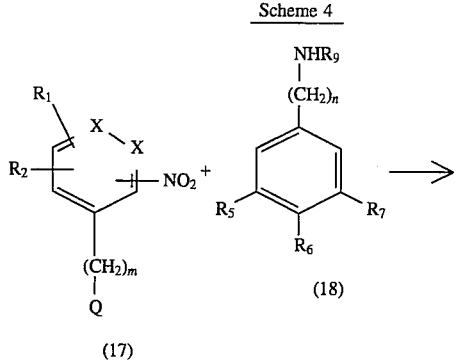

(17)         (18)

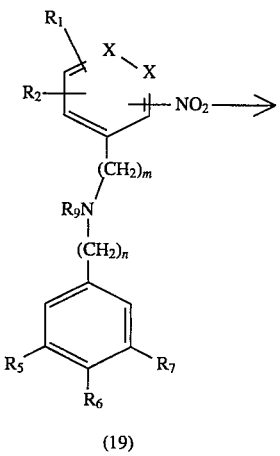

(19)

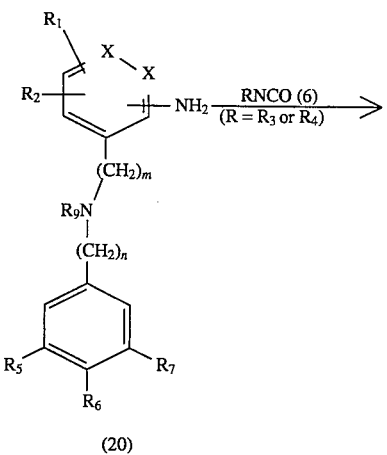

(20)

-continued
Scheme 4

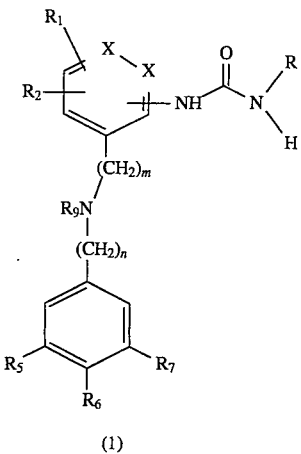

(1)

Alternatively, the compounds of formula (1) can be prepared by reducing a compound of formula (5) or (9a) with sodium boron hydride/boron trifluoride under ice-cooling in an ether solvent such as diethyl ether, tetrahydrofuran and dioxane to give a compound of formula (21a) or (21b), followed by reaction with an isocyanate RNCO of formula (6) in an organic solvent under ice-cooling or at a temperature up to room temperature.

The compound of formula (1) wherein $R_9$ is hydrogen 10 is reacted with an isocyanate of formula (6) in an organic solvent under ice-cooling or at a temperature up to room temperature to form a compound of formula (1) wherein $R_9$ is $CONHR_3$ ($R_3$ is as defined above).

The compound of formula (1) wherein $R_9$ is hydrogen is reacted with an acid chloride or an acid anhydride in an organic solvent in the presence of an acid binder under ice-cooling or at a temperature up to room temperature to form a compound of formula (1) wherein $R_9$ is alkylcarbonyl group.

The above reactions are shown in Scheme 5 below.

Scheme 5

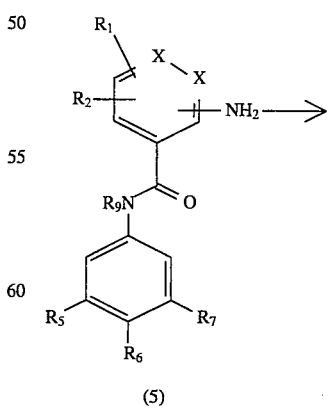

(5)

-continued
Scheme 5

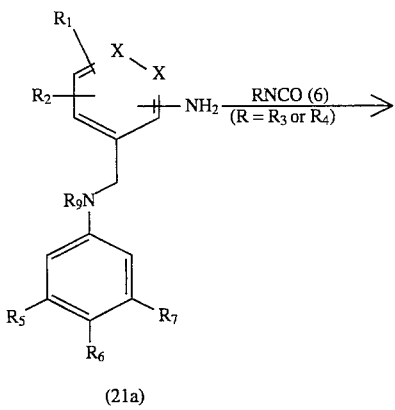

(21a)

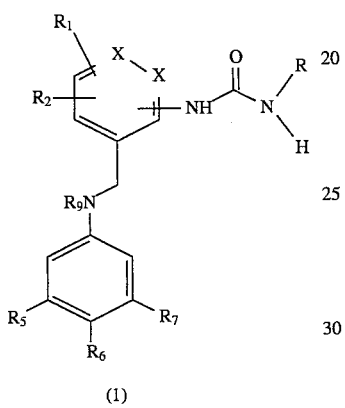

(1)

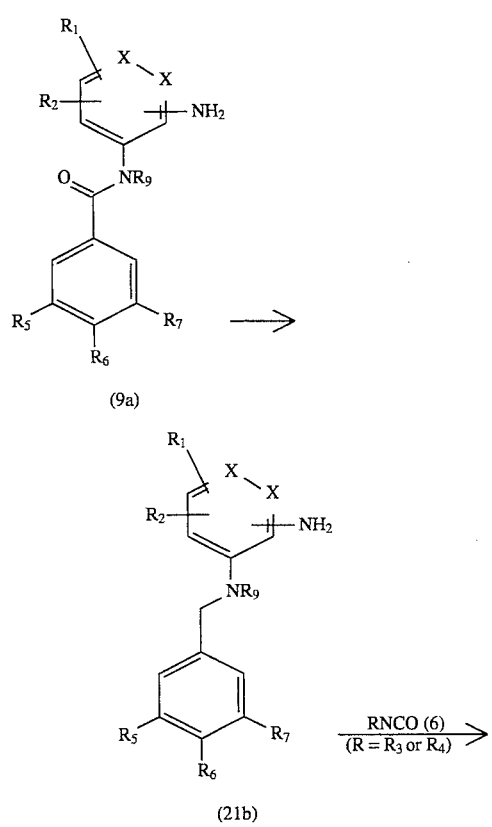

-continued
Scheme 5

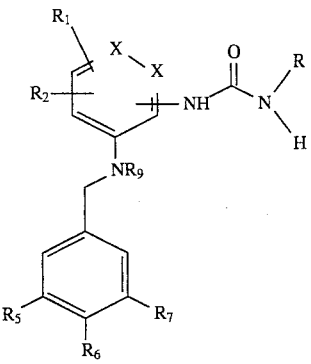

(1)

The compounds of formula (1) wherein A represents —O—(CH$_2$)$_3$— can be prepared by reacting a compound of formula (10) (R$_1$, R$_2$ and X are as defined above and Y is OH) with a compound of formula (22) (R$_5$, R$_6$, R$_7$ and Q are as defined above) at a temperature between room temperature and a reflux temperature in an organic solvent in the presence of an acid binder to give a compound of formula (23); reducing the compound of formula (23) with a reducing agent such as zinc, iron, tin and tin(II) chloride in an acid solution such as hydrochloric acid and acetic acid or alternatively subjecting the compound of formula (23) to catalytic hydrogenation using a catalyst such as palladium/carbon and platinum oxide in an alcohol solvent such as methanol and ethanol to give a compound of formula (24); and reacting the compound of formula (24) with an isocyanate RNCO of formula (6) in an organic solvent under ice-cooling or at a temperature up to room temperature.

Alternatively, the compounds of formula (1) are prepared by reacting a compound of formula (24) with phenyl chloroformate in an organic solvent under ice-cooling or at a temperature up to room temperature in the presence of an acid binder to give a compound of formula (25), followed by reaction with a compound of formula (13) in an organic solvent at a temperature of 0° to 150° C.

The above reactions are shown in Scheme 6 below.

Scheme 6

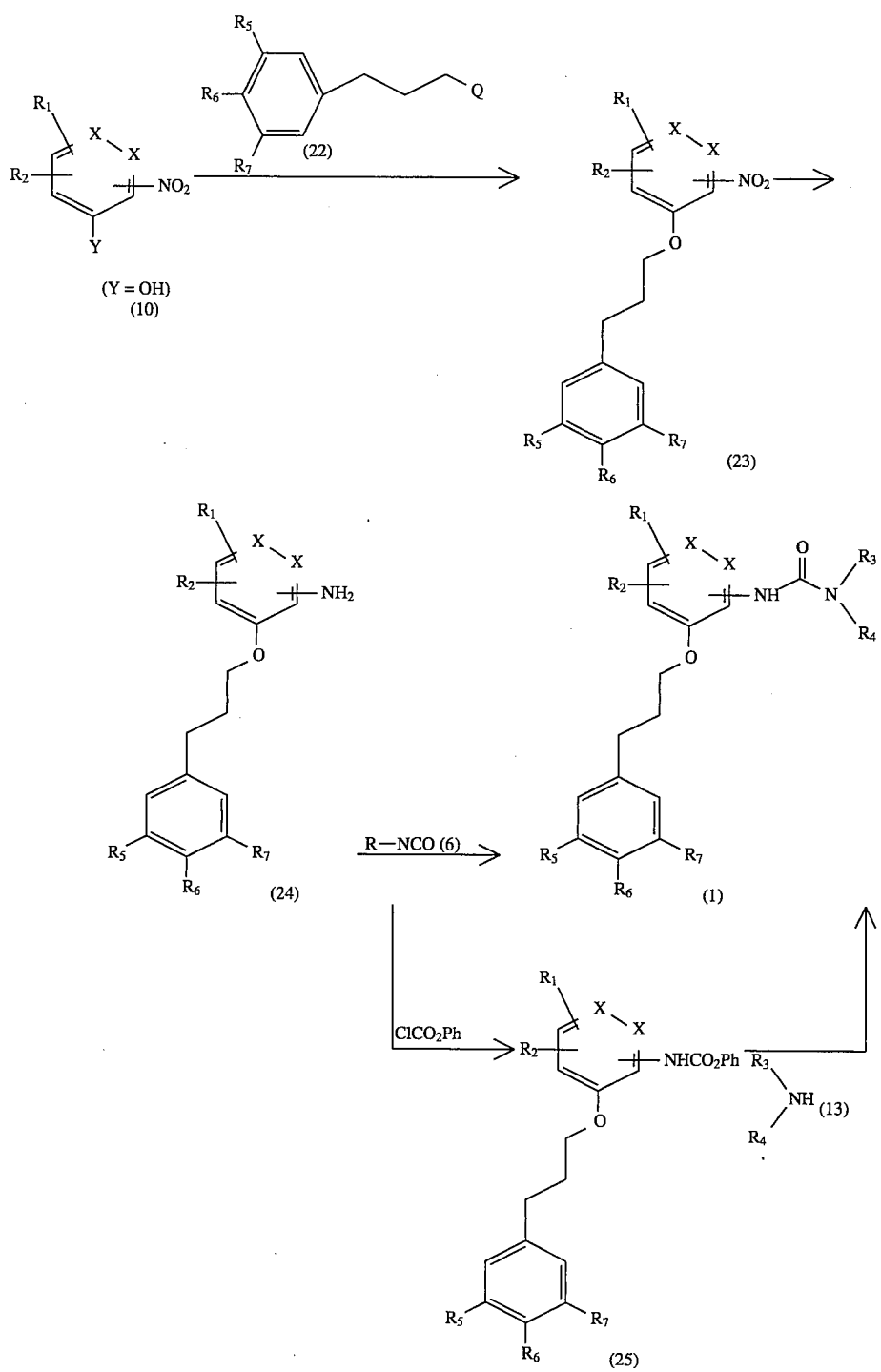

The organic-solvents used in each of the above-described reactions include aliphatic hydrocarbon solvents such as hexane, petroleum ether and cyclohexane, aromatic hydrocarbon solvents such as benzene, toluene and xylenes, halogenated hydrocarbon solvents such as methylene chloride, chloroform, carbon tetrachloride and dichloroethane, ether solvents such as ethyl ether, isopropyl ether, tetrahydrofuran and dioxane, ketone solvents such as acetone and methyl ethyl ketone, ethyl acetate, acetonitrile and N,N-dimethylformamide.

The acid binders used in each of the above-described reactions include e.g. inorganic basic substances such as sodium hydride, potassium hydroxide, sodium carbonate, potassium carbonate and organic basic substances including secondary amines such as diisopropylamine and tertiary amines such as triethylamine, methylmorpholine, pyridine.

Pharmaceutically acceptable salts of the compounds of formula (1) may be formed in conventional way. The acid addition salts may be formed for example by reaction of the base compound of formula (1) with a pharmaceutically acceptable inorganic acid such as hydrochloric, hydrobromic, hydroiodic, sulfuric and phosphoric acids or a pharmaceutically acceptable organic acid such as oxalic, maleic, fumaric, lactic, malic, citric, tartaric, benzoic and methanesulfonic acids.

The compounds of formula (1) according to the present invention possess both an ACAT inhibitory activity and an antioxidative activity, especially a protective ability against an oxidative modification of LDL. By the ACAT inhibitory activity, the present compounds can inhibit an absorption of cholesterol from the intestinal tracts, reduce a plasma cholesterol level and inhibit an accumulation of cholesteryl esters in the wall of blood vessels, atheroma lesion and macrophage. By the antioxidative activity, especially a protective activity against the oxidative modification of LDL, the present compounds can inhibit the formation and progression of atherosclerosis lesion and inducing its regression.

Thus, the compounds of the present invention are useful in the prophylaxis or treatment of hypercholesterolemia and atherosclerosis.

According to another aspect of the present invention, there is provided ACAT inhibitor comprising the compound of formula (1) or a pharmaceutically acceptable salt thereof.

In further aspects, the present invention provides a pharmaceutical composition for the prophylaxis or treatment of hypercholesterolemia or atherosclerosis, which comprises as an active ingredient the compound of formula (1) or a pharmaceutically acceptable salt thereof and a pharmaceutically acceptable carrier and/or excipient.

The compounds of the invention can usually be administered orally or parenterally in the form of a pharmaceutical preparation. The pharmaceutical preparations include tablets, capsules, troches, syrups, granules, powders, injections, suspensions and the like. It may be in bilayered or multilayered tablet with other drugs. The tablets may also be coated with a conventional coating to form, e.g., sugar-coated, enteric-coated or film-coated tablets.

In preparing solid preparations, additives such as lactose, refined sugar, crystalline cellulose, corn starch, calcium phosphate, sorbitol, glycin, carboxymethylcellulose, gum arabic, polyvinylpyrrolidone, hydroxypropylcellulose, polyethylene glycol, stearic acid, magnesium stearate and talc are employed.

A vegetable or synthetic wax or fat or a similar base is used in preparing the semi-solid preparations.

As additives in preparing the liquid preparations are used, for example, sodium chloride, sorbitol, glycerin, olive oil, almond oil, propylene glycol and ethyl alcohol.

The active ingredient is contained in the formulation in an amount of 0.0001–100% by weight, suitably 0.001–50% by weight in the case of formulations for oral administration and 0.0001–10% by weight in the case of formulations for injection based on the weight of the preparations.

Route and dosage of administration for the compounds of the invention are not specifically limited and are appropriately chosen depending upon form of the formulation, age and sex of the patient, severity of the disease and other factors. Daily dosage of the active ingredient is 0.01–1000 mg. No adverse toxicological effects are indicated at any of the above dosage ranges.

The invention is further illustrated by the following examples.

EXAMPLE 1

N-(4-dimethylaminophenyl)-2-(3-heptylureido)benzamide

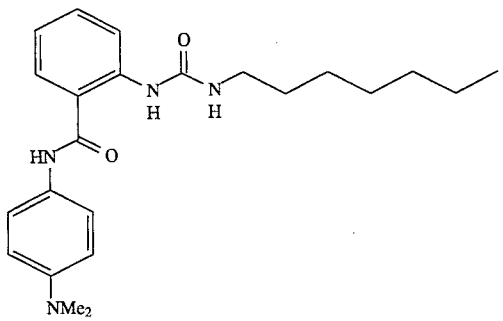

(1) A mixture of 2-nitrobenzoic acid (10 g) and thionyl chloride (11 ml) was heated under reflux for 2 hrs. and concentrated to dryness, the mixture was dissolved in dichloromethane (80 ml), triethylamine (10 ml) was added and a solution of N,N-dimethyl-1,4-phenylenediamine (9.0 g) in dichloromethane (10 ml) was added dropwise under ice-cooling and the mixture was stirred for 2 hours while returning slowly to room temperature. After distilling off the solvent, the reaction mixture was dissolved in ethyl acetate (800 ml), washed with water and then saturated saline, dried over anhydrous $MgSO_4$ to distill off the solvent. Crystallization of the residue from ethyl acetate afforded N-(4-dimethylaminophenyl)-2-nitrobenzamide (11 g, 64%).

(2) To a suspension of N-(4-dimethylaminophenyl)-2-nitrobenzamide (3.0 g) in ethanol (30 ml) was added a catalytic amount of 10% palladium/carbon and catalytic reduction was carried out at a pressure of 1–2.5 arms at room temperature for 4 hrs. After the filtration of 10 catalyst, the solvent was distilled off and crystallization of the residue from chloroform/ethyl acetate afforded N-(4-dimethylaminophenyl)-2-aminobenzamide (2.2 g, 79%).

(3) To a solution of N-(4-dimethylaminophenyl)-2-aminobenzamide (1.5 g) in dichloromethane (20 ml), heptyl isocyanate (2.4 g) was added under ice-cooling and the mixture was stirred overnight while returning slowly to room temperature. The solvent was distilled off and crystallization of the residue from chloroform/ethyl acetate afforded N-(4-dimethylaminophenyl)-2-(3-heptylureido)benzamide (1.6 g, 69%).

m.p. 178°–180° C.

$^1$H-NMR($\delta$ ppm, $CDCl_3$) 10.05(1H, s), 8.34(1H, d, J=8 Hz), 8.20(1H, s), 7.29–7.50(4H, m), 6.93(1H, t, J=7 Hz), 6.76(2H, d, J=9 Hz), 4.58(1H, t, J=5 Hz), 3.21–3.26(2H, m), 2.96(6H, s), 1.28–1.53(10H, m), 0.88(3H, t, J=6 Hz)

IR($cm^{-1}$) 3340, 2930, 1680, 1640, 1520, 1450, 1340, 1300, 1230, 820, 750

(4) To a solution of N-(4-dimethylaminophenyl)-2-(3-heptylureido)benzamide (0.70 g) in ethanol (10 ml) was added 4N-HCl/ethyl acetate solution (0.48 ml) under ice-cooling, and the mixture was concentrated to dryness to give N-(4-dimethylaminophenyl)-2-(3-heptylureido)benzamide monohydrochloride (0.77 g, 99%) as a non-crystallizable solid.

EXAMPLE 2

1-(4-dimethylaminophenyl)-1-[2-(3-heptylureido)benzyl]-3-heptylurea

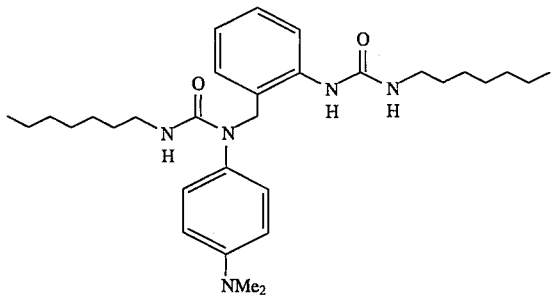

(1) To a suspension of lithium aluminium hydride (0.61 g) in THF (30 ml) was added dropwise under ice-cooling a solution of N-(4-dimethylaminophenyl)-2-aminobenzamide (2.0 g) in THF (20 ml) and the mixture was heated finder reflux. To this mixture was added dropwise small portions of water, the insolubles were filtered, and the solvent was distilled off. Purification of the residue by a silica gel column chromatography (hexane:ethyl acetate=1:1) and recrystallization from ethyl acetate/hexane afforded N-(2-aminobenzyl)-N',N'-dimethyl-1,4-phenylenediamine (1.1 g, 56%).

(2) To a solution of N-(2-aminobenzyl)-N',N'-dimethyl-1,4-phenylenediamine (0.6 g) in dichloromethane (10 ml) was added under ice-cooling heptyl isocyanate (0.4 g) and the mixture was stirred overnight while returning slowly to room temperature. The solvent was distilled off and the residue was purified by a silica gel column chromatography (chloroform:ethyl acetate=20:1) to give 1-(4-dimethylaminophenyl)-1-[2-(3-heptylureido)benzyl]-3-heptylurea as a non-crystallizable solid (0.55 g, 44%).

$^1$H-NMR($\delta$ ppm, CDCl$_3$) 9.31(s, 1H), 8.36(d, 1H, J=8 Hz), 7.20–7.25(m, 1H), 6.50–6.77(m, 6H), 5.17(t, 1H, J=5 Hz), 4.70(s, 2H), 4.33(t, 1H, J=6 Hz), 3.10–3.31(m, 4H), 2.96(s, 6H), 0.82–1.66(m, 26H)

IR(cm$^{-1}$) 2920, 2850, 1720, 1630, 1520, 1480, 1460, 1300, 1230

(3) An non-crystallizable solid of 1-(4-dimethylaminophenyl)-1-[2-(3-heptylureido)benzyl]-3-heptylurea monohydrochloride (0.49 g, 92%) was prepared from 1-(4-dimethylaminophenyl)-1-[2-(3-heptylureido)benzyl]-3-heptylurea (0.5 g) by similar procedure as mentioned in Example 1 (4).

EXAMPLE 3

N-(4-dimethylaminophenyl)-N-geranyl-2-(3-heptylureido)benzamide

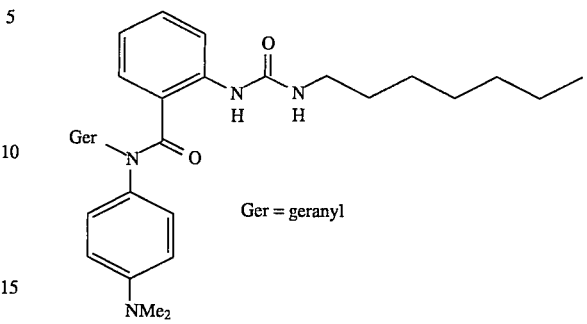

Ger = geranyl (1) A mixture of 2-nitrobenzoic acid (2.3 g) and thionyl chloride (2.5 ml) was heated under reflux for 2 hrs., concentrated to dryness and the mixture was dissolved in dichloromethane (20 ml). To the solution was added triethylamine (2.3 ml) and then added dropwise under ice-cooling a solution of N,N-dimethyl-N'-geranyl-1,4-phenylenediamine (4.0 g) in dichloromethane (10 ml). The mixture was stirred for 2 hrs. while returning slowly to room temperature. The reaction solution was washed with water and saturated saline and dried over anhydrous MgSO$_4$. The solvent was distilled off. The residue was purified by a silica gel column chromatography (hexane:ethyl acetate=3:1) to give N-(4-dimethylaminophenyl)-N-geranyl-2-nitrobenzamide (5.6 g, 95%) as an oily product.

(2) N-(4-dimethylaminophenyl)-N-geranyl-2-nitrobenzamide (2.5 g) was dissolved in ethanol (35 ml), to the solution was added 1N-aqueous HCl (6.5 ml) and iron powder (1.3 g), and the mixture was stirred under heat for 2 hrs. After filtering the insolubles, distilling off the solvent, and neutralizing with 10% sodium hydroxide solution, the mixture was extracted with ethyl acetate, washed with water and saturated saline and dried over anhydrous MgSO$_4$. The solvent was distilled off. The residue was purified by a silica gel column chromatography (hexane:ethyl acetate=3:1) to give N-(4-dimethylaminophenyl)-N-geranyl-2-aminobenzamide 1.3 g (58%) as an oily product.

(3) To a solution of N-(4-dimethylaminophenyl)-N-geranyl-2-aminobenzamide (0.8 g) in dichloromethane (10 ml) was added under ice-cooling heptyl isocyanate (0.56 g) and the mixture was stirred overnight while returning slowly to room temperature. After distilling off the solvent, the 10 residue was purified by a silica gel column chromatography (hexane:ethyl acetate=3:1) to give N-(4-dimethylaminophenyl)-N-geranyl-2-(3-heptylureido)benzamide (0.98 g, 89%) as an oily product.

$^1$H-NMR($\delta$ ppm, CDCl$_3$) 8.55(1H, br.s), 8.04(1H, d, J=8 Hz), 7.14(1H, br.s), 6.46–6.81(6H, m), 5.33(1H, br.s), 5.03–5.05(1H, m), 4.77(2H, br.s), 4.43(1H, br.s), 3.21–3.27(2H, m), 2.88(6H, s), 0.87–2.13(26H, m)

IR(cm$^{-1}$) 3350, 2920, 1620, 1590, 1520, 1450, 1230

(4) A non-crystallizable solid of N-(4-dimethylaminophenyl-N-geranyl-2-(3-heptylureido)benzamide monohydrochloride (0.95 g, 98%) was prepared from N-(4-dimethylaminophenyl)-N-geranyl-2-(3-heptylureido)benzamide (0.91 g) by similar procedure as mentioned in Example 1 (4).

EXAMPLE 4

1-[2-[N-(4-dimethylaminophenyl)-N-geranylaminomethyl]phenyl]-3-heptylurea

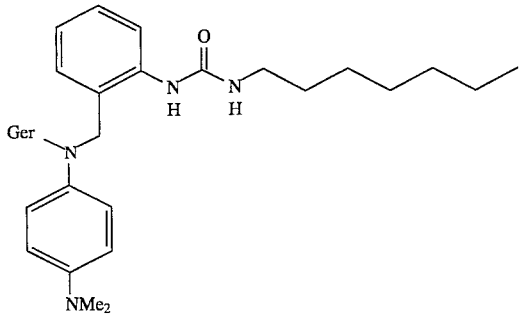

(1) N,N-dimethyl-N'-geranyl-N'-(2-nitrobenzyl)-1,4-phenylenediamine (1.0 g) was dissolved in ethanol (20 ml), to the solution was added 1N-aqueous HCl (2.5 ml) and iron powder (0.6 9), and the mixture was stirred under heat for 2 hrs. After filtration of the insolubles, distilling off the solvent and neutralizing with 10% sodium hydroxide solution, the mixture was extracted with ethyl acetate, washed with water and saturated saline, dried over anhydrous MgSO$_4$, and the solvent was distilled off. Purification of the residue by a silica gel column chromatography (hexane:ethyl acetate= 4:1) afforded N-(2-aminobenzyl)-2-geranyl-N,N'-dimethyl-1,4-phenylenediamine (0.58 g, 62%) as an oily product.

(2) To a solution of N-(2-aminobenzyl)-N-geranyl-N',N'-dimethyl-1,4-phenylenediamine (0.54 g) in dichloromethane (10 ml) was added under ice-cooling heptyl isocyanate (0.3 g) and the mixture was stirred overnight while returning slowly to room temperature. After distilling off the solvent, the residue was purified by a silica gel column chromatography (hexane:ethyl acetate=3:1) to give 1-[2-[N-(4-dimethylaminophenyl)-N-geranylaminomethyl]phenyl]-3-heptylurea (0.62 g, 85%) as an oily product.

$^1$H-NMR($\delta$ ppm, CDCl$_3$) 8.82(1H, d, J=12 Hz),7.75(1H, t, J=8 Hz), 6.69–7.26(7H, m), 4.99–5.20(2H, m), 4.32–4.35(1H, m), 4.16(2H, s), 3.59(2H, d, J=6 Hz), 3.12–3.18(2H,m), 2.88(6H, s), 0.86–2.04(26H, m)

IR(cm$^{-1}$) 3320, 2930, 2850, 1650, 1550, 1520, 1450, 1240

(3) A non-crystallizable solid of 1-[2-[N-(4-dimethylaminophenyl)-N-geranylaminomethyl]phenyl]-3-heptylurea dihydrochloride (0.7 g, 99%) was prepared from 1-[2-[N-(4-dimethylaminophenyl)-N-geranylaminomethyl]phenyl-3-heptylurea (0.6 g) by similar procedure as mentioned in Example 1 (4).

EXAMPLE 5

1-[2-[N-geranyl-N-(3,4-methylenedioxyphenyl)aminomethyl]phenyl]-3-heptylurea

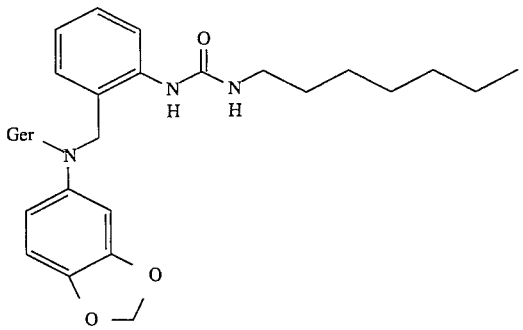

The title compound was prepared by similar procedure as mentioned in Example 4. $^1$H-NMR($\delta$ ppm, CDCl$_3$) 8.29(1H, d, J=19 Hz), 7.89(1H, t, J=9 Hz), 6.43–7.28(6H, m), 5.91(2H, d, J=3 Hz), 4.97–5.18(2H, m), 4.32–4.35(1H, m), 4.16(2H, s), 3.62(2H, d, J=6 Hz), 3.12–3.18(2H, m), 0.86–2.15(26H, m)

IR(cm$^{-1}$) 3340, 2940, 2850, 1640, 1560, 1510, 1500, 1220, 1050

EXAMPLE 6

N-[2-(3-heptylureido)phenyl]-3,5-di-t-butyl-4-hydroxybenzamide and

N-[2-(3-heptylureido)phenyl]-3,5-di-t-butyl-4-[(N-heptyl)carbamoyloxy]benzamide

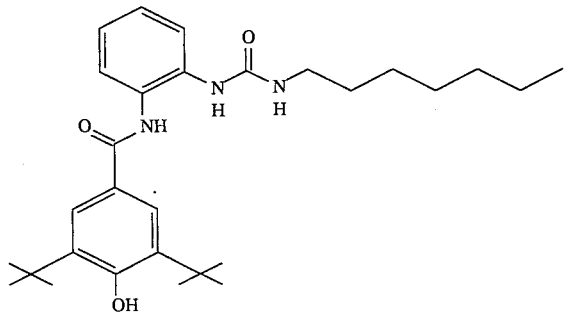

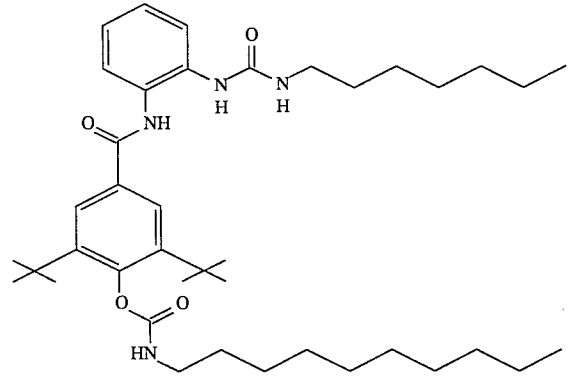

(1) To a solution of 3,5-di-t-butyl-4-hydroxybenzoic acid (5.0 g) in methylene chloride (20 ml) was added dicyclohexylcarbodiimide (2.17 g) and the mixture was stirred overnight at room temperature. Subsequently, triethylamine (2.1 ml), 4-dimethylaminopyridine (0.37 g) and o-phenylenediamine (1.08 g) were added and the mixture was stirred overnight at room temperature. The insolubles was filtered off and the filtrate was concentrated to dryness. The residue was purified by a silica gel column chromatography (chloroform:ethyl acetate=20:1) and crystallized from diisopropyl ether to give N-(2-aminophenyl)-3,5-di-t-butyl-4-hydroxybenzamide (1.10 g, 32%).

(2) A mixture of n-caprylic acid (0.32 g), diphenylphosphoryl azide (0.53 ml) and triethylamine (0.34 ml) was stirred in toluene (5 ml) at room temperature for 3 hrs. and additional 2 hrs. at 80°–90° C. To the mixture was added under ice-cooling N-(2-aminophenyl)-3,5-di-t-butyl-4-hydroxybenzamide (0.51 g) and the mixture was stirred for 3 hrs. while returning slowly to room temperature. The solvent was distilled off and the residue was purified by a silica gel column chromatography (chloroform:ethyl acetate =10:1) to give N-[2-(3-heptylureido)phenyl]-3,5-di-t-butyl-4-hydroxybenzaldehyde (0.25 g, 35%), m.p.95°–100° C. $^1$H-NMR($\delta$ ppm, CDCl$_3$) 9.93(1H, br.s), 7.84(2H, s), 7.64(1H, d, J=7 Hz), 7.09–7.04(2H, m), 6.87(1H, t, J=7 Hz), 6.62(1H, br.d), 5.64(1H, s), 5.28(1H, br.s), 3.09(2H, q-like, J=7 Hz), 1.48(18H, s), 1.44–1.20(10H, m), 0.85(3H, t, J=7 Hz)

IR(cm$^{-1}$) 3336, 2956, 2928, 1638, 1600, 1561, 1516, 1430, 1307, 1236, 1114, 751 and N-[2-(3-heptylureido)phenyl]-3,5-di-t-butyl-4-[(N'heptyl)carbamoyloxy]benzamide (0.28 g, 30%) as crystals, respectively, m.p.120°–122° C. $^1$H-NMR($\delta$ ppm, CDCl$_3$) 9.87(1H, br.s), 7.93(2H, s), 7.74(1H, d, J=8 Hz ), 7.08 ( 1H, t, J=8 Hz ), 6.98–6.90(2H, m), 6.84(1H, br.s), 5.17(1H, br.t), 3.29(2H, q-like, J=6 Hz), 3.09(2H, q-like, J=6 Hz), 1.43–1.20(38H, m), 0.90(3H, t, J=6 Hz), 0.86 (3H, t, J=6 Hz)

IR(cm$^{-1}$) 3374, 2954, 2930, 1712, 1680, 1644, 1544, 1520, 1422, 1246, 1199, 752

EXAMPLE 7

N-[2-(3-(2,2-diphenylethyl)ureido]phenyl]-3,5-di-t-butyl-4-hydroxybenzamide

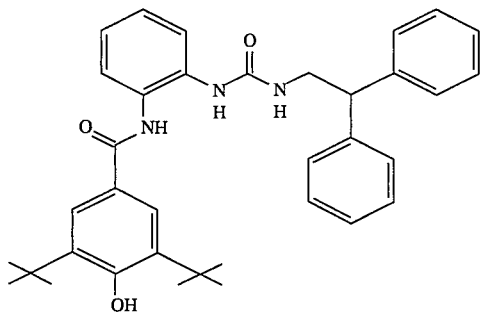

The title compound was prepared by similar procedure as mentioned in Example 6, using 3,3-diphenylpropionic acid instead of n-caprylic acid.

m.p.198°–200° C. $^1$H-NMR($\delta$ ppm, CDCl$_3$) 9.74(1H, s), 7.83(2H, s), 6.96(1H, s), 6.54–7.49(14H, m), 5.64(1H, s), 5.18–5.20(1H, m), 4.15(1H, t, J=8 Hz), 3.79(2H, dd, J=8, 6 Hz), 1.48(18H, s)

IR(cm$^{-1}$) 3620, 3314, 2958, 1639, 1545, 1431, 1309, 1233, 755, 701

EXAMPLE 8

N-[2-(3,3-dibenzylureido)phenyl]-3,5-di-t-butyl-4-hydroxybenzamide

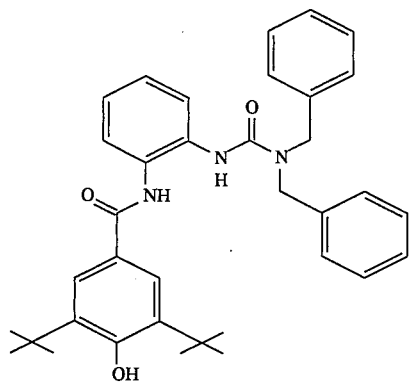

(1) N-(2-aminophenyl)-3,5-di-t-butyl-4-hydroxybenzamide (0.85 g) and diisopropylamine (0.39 ml) were suspended in dichloromethane (20 ml) and a solution of phenyl chloroformate (16.8 g) in dichloromethane (30 ml) was added dropwise under ice-cooling. After stirring the mixture overnight, the reaction solution was washed with water, saturated saline, dried over anhydrous MgSO$_4$ and the solvent was distilled off. Purification of the residue by a silica gel column chromatography (chloroform:ethyl acetate=10:1) followed by crystallization from hexane/ethyl acetate afforded phenyl N-[2-(3,5-di-t-butyl-4-hydroxybenzoylamino)phenyl]carbamate (12.6 g, 49%).

(2) Phenyl N-[2-(3,5-di-t-butyl-4-hydroxybenzoylamino)phenyl]carbamate (1.6 g) and dibenzylamine (0.7 g) were dissolved in benzene (10 ml) and stirred at 70°–80°0 C. for 2 hrs. The reaction solution was washed with 2N sodium hydroxide, saturated ammonium chloride solution, dried over anhydrous NaSO$_4$ and the solvent was distilled off. Purification of the residue by a silica gel column chromatography followed by crystallization from ether afforded N-[2-(3,3-dibenzylureido )phenyl]-3,5-di-t-butyl-4-hydroxybenzamide (0.47 g, 23%).

m.p.187°–189° C.

$^1$H-NMR($\delta$ ppm, CDCl$_3$) 9.53(1H, s), 7.79(2H, s), 7.56(1H, dd, J=8, 1 Hz), 7.25–7.14(11H, m), 7.10–6.90(3H, m), 5.59(1H, s), 4.57(4H, s), 1.45(18H, s)

IR(cm⁻¹) 3620, 3220, 1638, 1602, 1524, 1500, 1454, 1436, 1381, 1238, 748, 700

EXAMPLE 9

1-[N-2-(3,5-di-t-butyl-4-hydroxybenz-amide)phenyl]carbamoyl]-4-methylpiperazine

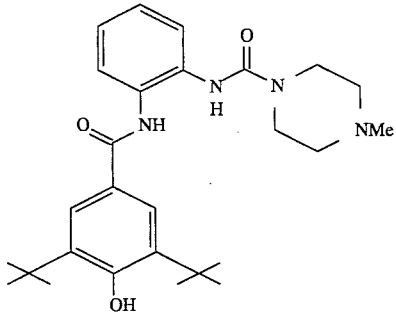

The title compound was prepared by similar procedure as mentioned in Example 8, using N-methylpiperazine instead of dibenzylamine.

m.p. 169°–171° C.

¹H-NMR (δ ppm, CDCl₃) 9.51(1H, s), 7.99(1H, s), 7.80(2H, s), 7.28–7.24(1H, m), 7.13(1H, d, J=8 Hz), 6.87–6.73(2H, m), 5.64(1H, s), 3.53(4H, t, J=5 Hz), 2.39(4H, t, J=5 Hz), 1.52(18H, s)

IR(cm⁻¹) 3630, 3540, 3310, 2960, 2800, 1645, 1600, 1530, 1435, 1305, 1260, 1240, 1110, 1005, 755

EXAMPLE 10

N-[2-(3-cyclopentyl)ureido]phenyl-3,5-di-t-butyl-4-hydroxybenzamide

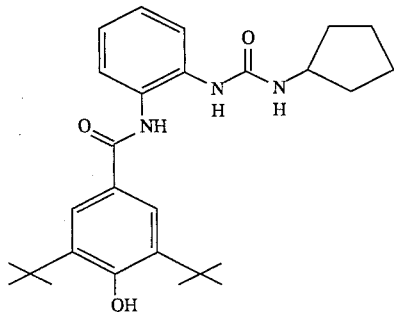

The title compound was prepared in similar procedure as mentioned in Example 8, using cyclopentylamine instead of dibenzylamine.

m.p. 195°–197° C.

¹H-NMR (δ ppm, CDCl₃) 9.65(1H, s), 7.83(2H, s), 7.67(1H, d, J=7 Hz ), 7.12–7.06 (1H, m), 6.96–6.90(2H, m), 6.86–6.80(1H, m), 5.63(1H, s), 4.96(1H, d, J=7 Hz), 4.08 –3.94 (1H, m ), 1.96–1.81(2H, m), 1.72–1.02(6H, m), 1.49(s, 18H)

3640, 3630, 3330, 2960, 1640, 1580, 1530, 1440, 1320, 1228, 896, 750

EXAMPLE 11

N-[2-(3-adamantyl)ureido]phenyl-3,5-di-t-butyl-4-hydroxybenzamide

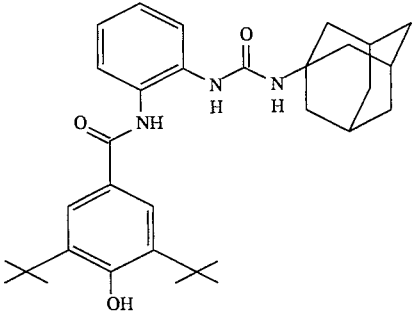

The title compound was prepared in similar procedure as mentioned in Example 8, using 1-adamantylamine instead of dibenzylamine.

m.p. 204°–205° C.

¹H-NMR (δ ppm, CDCl₃) 9.79(1H, s), 7.87(2H, s), 7.63(1H, dd, J=8 Hz, 2 Hz), 7.07(1H, ddd, J=8 Hz, 8 Hz, 2 Hz), 6.90(1H, ddd, J=8 Hz, 8 Hz, 2 Hz), 6.80–6.73(2H, m), 5.63(1H, s), 4.80(1H, s), 2.00(3H, br.s), 1.87(6H, d, J=2 Hz), 1.61(1H, d, J=3 Hz), 1.50(18H, s)

IR(cm⁻¹) 3630, 3360, 3310, 2915, 1685, 1640, 1600, 1555, 1520, 1485, 1435, 1300, 1240, 755

EXAMPLE 12

N-[2-[3-benzyl-3-(2-pyridylmethyl)ureido]phenyl]-3,5-di-t-butyl-4-hydroxybenzamide

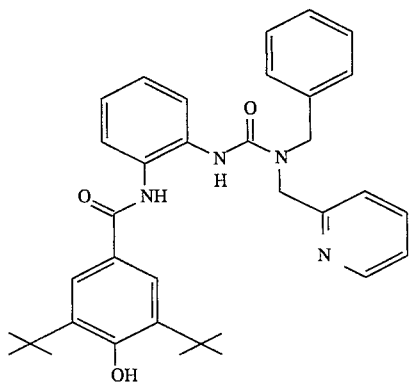

The title compound was prepared in similar procedure as mentioned in Example 8, using 2-(N-benzylaminomethyl)pyridine instead of dibenzylamine.

m.p. 162°–163° C.

¹H-NMR (δ ppm, CDCl₃) 9.85 (1H, br.s), 8.51(1H, d, J=4 Hz), 7.93–7.86(3H, m), 7.56(1H, ddd, J=8 Hz, 8 Hz, 2 Hz), 7.25–7.07(10H, m), 6.90(1H, d, J=7 Hz), 5.56(1H, s), 4.67(2H, s), 4.42(2H, br.s), 1.44(18H, s)

IR(cm⁻¹) 3640, 3500, 3270, 2960, 1645, 1600, 1540, 1480, 1430, 1314, 1236, 764

EXAMPLE 13

N-[2-(3-heptyl-3-methyl)ureido]phenyl-3,5-di-t-butyl-4-hydroxybenzamide

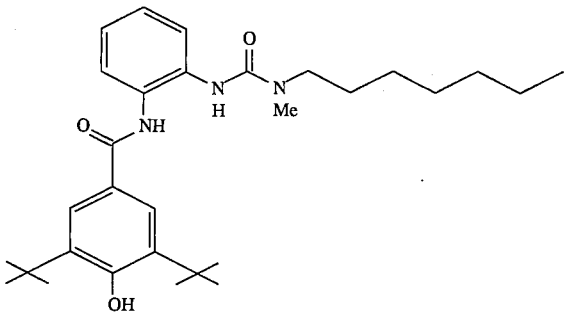

The title compound was prepared in similar procedure as mentioned in Example 8, using N-methylheptylamine instead of dibenzylamine.

m.p. 156°–157° C.

$^1$H-NMR (δ ppm, CDCl$_3$) 9.43(1H, br.s), 7.84(2H, s), 7.55–7.50(1H, m), 7.29–7.24(1H,m) 7.17–7.11(1H, m), 7.06–7.00(2H, m), 5.62(1H, s), 3.32(2H, d, J=8 Hz), 2.99(3H, s), 1.58–1.50(2H, m), 1.50(18H, m), 1.31–1.16(8H, m), 0.86(3H, t, J=7 Hz)

IR(cm$^{-1}$) 3625, 3605, 3260, 2960, 2930, 1635, 1600, 1520, 1490, 1435, 1310, 1235, 750

EXAMPLE 14

1-[2-[N-(3,5-di-t-butyl-4-hydroxybenzyl)aminomethyl]phenyl]-3-heptylurea

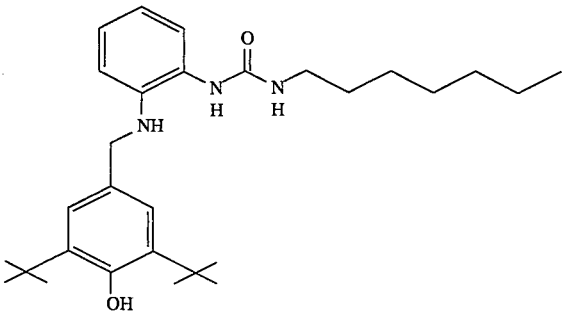

(1) To a suspension of sodium borohydride (2.72 g) in tetrahydrofuran (80 ml) was added dropwise under ice-cooling BF3, Et20 (8.86 ml) and the mixture was stirred for 30 minutes. To this mixture was added by portions N-(2-aminophenyl )-3,5-di-t-butyl-4-hydroxybenzamide (3.06 g ) and the mixture was stirred overnight while returning slowly to room temperature. 6N hydrochloric acid war added and the mixture was heated under reflux for 30 minutes, the solvent was distilled off and the residue was placed into water, neutralized with sodium hydrogen carbonate, extracted with ethyl acetate, washed with water and saturated saline and dried over anhydrous MgSO$_4$. The solvent was distilled off and the residue was purified by a silica gel column chromatography (hexane:ethyl acetate=4:1) to give (2-aminophenyl)-3,5-di-t-butyl-4-hydroxybenzylamine (2.00 g, 68%) as crystals.

(2) n-caprylic acid (0.15 g), diphenylphosphoryl azide (0.28 ml) and triethylamine (0.21 ml) were stirred in toluene (5 ml) at room temperature for 3 hrs. and additional 2 hrs. at 80°–90° C. To this mixture was added under ice-cooling a solution of (2-aminophenyl)-3,5-di-t-butyl-4-hydroxybenzylamine (0.34 g) in toluene (5 ml) and the mixture was stirred overnight while returning slowly to room temperature. The solvent was distilled off and the residue was purified by a silica gel column chromatography (chloroform:ethyl acetate=20:1) to give 1-[2-[N-(3,5-di-t-butyl-4-hydroxybenzyl)aminomethyl]phenyl]-3-heptylurea (0.31 g, 64%) as crystals.

m.p.135°–138° C.

$^1$H-NMR (δ ppm, CDCl$_3$) 9.21(1H, t, J=7 Hz), 7.12(2H, s), 7.11(1H, d, J=7 Hz), 6.78(1H, d, J=7 Hz), 6.71(1H, t, J=7 Hz), 5.53(1H, br.s), 5.20(1H, s), 4.60(1H, br.t), 4.45(1H, br.s), 4.17(2H, br.s), 3.16(2H, q-like, J=7 Hz), 1.50–1.40(20H, m), 1.35–1.20(8H, m), 0.86(3H, t, J=7 Hz)

IR(cm$^{-1}$) 3634, 3324, 2954, 2928, 1639, 1568, 1504, 1432, 1236, 746

EXAMPLE 15

1-[2-[N-acetyl-N-(3,5-di-t-butyl-4-hydroxybenzyl)aminomethyl]phenyl]-3-heptylurea

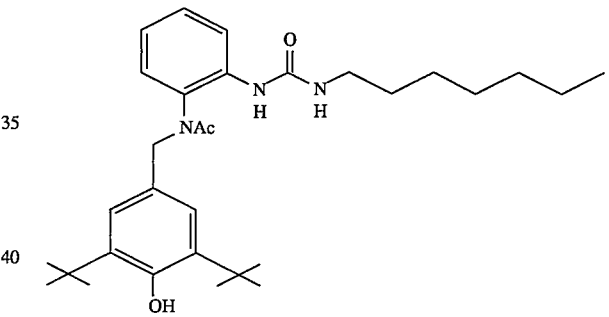

1-[2-[N-(3,5-di-t-butyl-4-hydroxybenzyl)aminomethyl]phenyl]-3-heptylurea (0.23 g), 4-dimethylaminopyridine (0.02 g) and triethylamine (0.14 ml) were dissolved in toluene (5 ml) and acetic anhydride (0.05 ml) was added under ice-cooling. The mixture was stirred overnight while returning slowly to room temperature. The solvent was distilled off, ethyl acetate was added, the mixture was washed with 1N hydrochloric acid, an aqueous sodium hydrogen carbonate solution, water, saturated saline and dried over anhydrous MgSO$_4$. The solvent was distilled off and the residue was crystallized from hexane to give 2-[2-[N-acetyl-N-(3,5-di-t-butyl-4-hydroxybenzyl)aminomethyl]phenyl]-3-heptylurea (0.24 g, 96%).

m.p.125°–128° C.

$^1$H-NMR (δ ppm, CDCl$_3$) 8.40(1H, d, J=8 Hz), 7.36(1H, br.s), 7.29(1H, t, J=8 Hz), 6.95(2H, s), 6.85(1H, t, J=8 Hz), 6.69(1H, d, J=8 Hz), 5.86(1H, br.s), 5.19(1H, s), 5.03(1H, br.d, J=14 Hz), 4.46(1H, br.d, J=14 Hz), 3.16(2H, m), 1.84(3H, s), 1.35(18H, s), 1.40°–1.20(10H, m), 0.86(3H, t, J=7 Hz)

IR(cm$^{-1}$) 3360, 2954, 2928, 1692, 1627, 1548, 1456, 1286, 1231, 1101, 749

EXAMPLE 16

N-[2-3-heptylureido)phenyl]-N-methyl-3,5-di-t-butyl-4-hydroxybenzamide

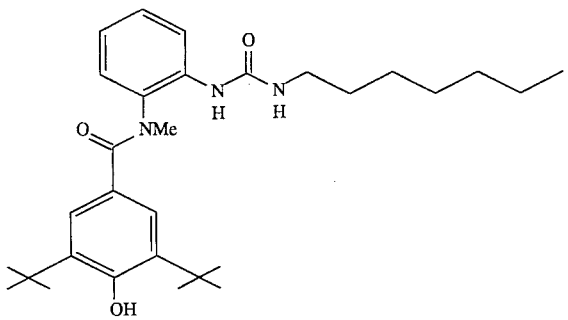

(1) n-caprylic acid (1.44 g), diphenylphosphoryl azide (2.80 ml) and triethylamine (2.09 ml) were stirred in toluene (10 ml) at room temperature for 3 hrs. and additional 2 hrs. at 80°–90° C. To the ice-cooled mixture was added N-methyl-1,2-phenylenediamine (1.22 g) and the mixture was stirred overnight while returning slowly to room temperature. The solvent was distilled off and the residue was purified by a silica gel column chromatography (hexane-:ethyl acetate=1:1) to give 2-(3-heptyl)ureidophenyl 3,5-di-t-butyl-4-hydroxybenzoate (1.58 g, 63%) as crystals. The crystals (0.50 g), 3,5-di-t-butyl-4-hydroxybenzoic acid (0.50 g) and dicyclohexylcarbodiimide (0.42 g) was stirred in dichloromethane (5 ml) at room temperature overnight. The insolubles were filtered off and the solvent was distilled off. The residue was crystallized from hexane to give N-[2-(3-heptylureido)phenyl]-N-methyl-3,5-di-t-butyl-4-hydroxybenzamide (2.31 g, 93%).

m.p. 193°–196° C.

$^1$H-NMR (δ ppm, CDCl$_3$) 8.38(1H, d, J=7 Hz), 8.14(1H, br.s), 7.11(1H, t, J=7 Hz), 6.96(2H, br.s), 6.89(1H, br.s), 6.64(1H, t, J=7 Hz), 6.54(1H, t, J=7 Hz), 5.22(1H, s), 3.35(2H, m), 3.17(3H, br.s), 1.50–1.25(10H, m), 1.14(18H, s), 0.89(3H, t, J=9 Hz)

IR(cm$^{-1}$) 3358, 2951, 2926, 1697, 1617, 1544, 1455, 1416, 1373, 1300, 1235, 1102

EXAMPLE 17

N-[2-(3-cyclopentyl)ureido-5-methoxyphenyl]-3,5-di-t-butyl-4-hydroxybenzamide

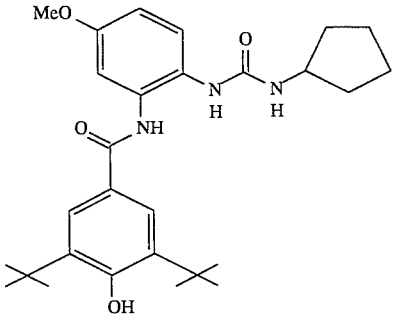

(1) To a solution of 4-methoxy-2-nitroaniline (15.0 g) and diisopropylamine (16.2 ml) in dichloromethane (300 ml) was added dropwise under ice-cooling a solution of phenylchloroformate (16.8 g) in dichloromethane (30 ml). The reaction solution was stirred at room temperature overnight, washed with water and saturated saline and dried over anhydrous MgSO$_4$. The solvent was distilled off. Crystallization of the residue from hexane gave phenyl 4-methoxy-2-nitrophenylcarbamate (12.6 g, 49.1%) as crystals.

(2) Phenyl 4-methoxy-2-nitrophenylcarbamate (1.1 g) and cyclopentylamine (0.37 g) were dissolved in xylene (10 ml) and the solution was heated under reflux for 2 hrs. After allowing the reaction solution to cool, the crystals formed was filtered, washed with xylene, and dried to give 1-(4-methoxy-2-nitrophenyl)-3-cyclopentylurea (0.97 g, 87%) as crystals.

(3) To a suspension of 1-(4-methoxy-2-nitrophenyl)-3-cyclopentylurea (0.96 g) in ethanol (15 ml) was added a catalytic amount of 10% palladium/carbon to carry out catalytic reduction at a pressure of 1–2.5 atms at room temperature for 2 hrs. The catalyst was filtered off, the solvent was distilled off and crystallization of the residue from benzene and hexane afforded 1-(2-amino-4-methoxyphenyl)-3-cyclopentylurea (0.79 g, 93%).

(4) 1-(2-amino-4-methoxyphenyl)-3-cyclopentylurea (0.66 g), 1-ethyl-3-(3-dimethylaminopropyl)carbodiimide monohydrochloride (0.59 g) and 3,5-di-t-butyl-4-hydroxybenzoic acid (0.78 g) was dissolved in dichloromethane (70 ml) and stirred overnight at room temperature. The reaction solution was washed with water and saturated saline and dried over anhydrous MgSO$_4$. The solvent was distilled off and crystallization of the residue from ethyl acetate afforded N-[2-(3-cyclopentyl)ureido-5-methoxyphenyl]-3,5-di-t-butyl-4-hydroxybenzamide (0.92 g, m.p.204°–205° C.

$^1$H-NMR (δ ppm, CDCl$_3$), 9.27(1H, br.s), 7.79(2H, s), 7.63(1H, br.s), 6.91(1H, d, J=9 Hz), 6.58(1H, dd, J=9 Hz, 3 Hz), 6.33(1H, br.s), 5.63(1H, s), 4.66(1H, d, J=7 Hz), 3.95–4.07(1H, m), 3.77(3H, s), 1.85–1.92(2H, m), 1.51–1.58(4H, m), 1.48(18H, s), 1.21–1.30(2H, m)

IR(cm$^{-1}$) 3630, 3300, 2950, 1650, 1540, 1320, 1240, 1220, 1070, 1040

EXAMPLE 18

N-[2-(3-heptylureido)-5-methoxyphenyl]-3,5-di-t-butyl-4-hydroxybenzamide

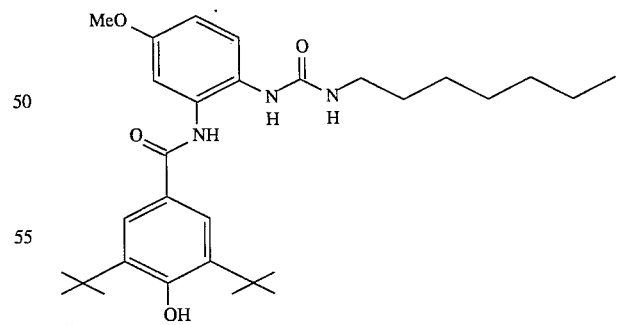

The title compound was prepared by similar procedure as mentioned in Example 17, using heptylamine instead of cyclopentylamine.

m.p.150°–151° C.

$^1$H-NMR (δ ppm, CDCl$_3$) 9.35(1H, br.s), 7.79(2H, s) 7.67(1H, br.s), 6.86(1H, d, J=9 Hz), 6.57(1H, dd, J=9 Hz, 3 Hz) 6.36(1H, br.s), 5.64(1H, s), 4.82(1H, s), 3.79(3H, s), 3.11–3.16(2H, m), 1.48(18H, s), 1.20–1.26(10H, m), 0.84(3H, t, J=7 Hz)

IR(cm$^{-1}$) 3400, 2880, 2870, 1640, 1560, 1520, 1430, 1300, 1240

EXAMPLE 19

N-[2-(3-adamantylureido)-5-methoxyphenyl]-3,5-di-t-butyl-4-hydroxybenzamide

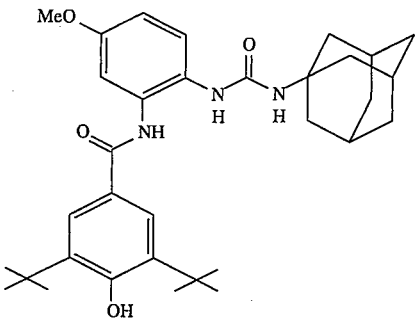

The title compound was prepared by similar procedure as mentioned in Example 17, using 1-adamantylamine instead of cyclopentylamine.

m.p.198°–199° C.

$^1$H-NMR (δ ppm, DMSO) 10.38(1H, br.s), 7.78(1H, br.s), 7.73(2H, s), 7.55(1H, br.s), 7.24(1H, d, J=2 Hz), 7.15(1H, d, J=9 Hz), 6.69(1H, dd, J=9 Hz, 2 Hz), 6.26(1H, br.s), 3.72(3H, s), 1.99–2.05(3H, m), 1.90–1.99(6H, m), 1.53–1.68(6H, m), 1.43(18H, s)

IR(cm$^{-1}$) 3400, 2880, 2860, 1680, 1640, 1520, 1430, 1300, 1280, 1240

EXAMPLE 20

N-[2-(3,3-dibenzylureido)-5-methoxyphenyl]-3,5-di-t-butyl-4-hydroxybenzamide

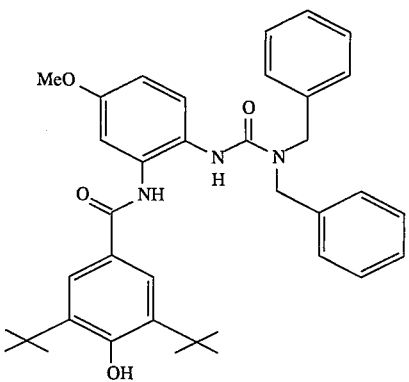

The title compound was prepared by similar procedure as mentioned in Example 17, using dibenzylamine instead of cyclopentylamine.

$^1$H-NMR (δ ppm, CDCl$_3$) 9.82(1H, s), 7.86(2H, s), 7.15–7.36(11H, m), 6.99(1H, s), 6.68(1H, d, J=9 Hz), 6.54(1H, dd, J=9 Hz, 3 Hz), 5.59(1H, s), 4.56(4H, s), 3.62(3H, s), 1.44(18H, s)

IR(cm$^{-1}$) 3600, 3250, 2950, 1640, 1600, 1520, 1500, 1450, 1430, 1300, 1240, 700

EXAMPLE 21

N-[2-(3-heptyl-3-methylureido)-5-methoxyphenyl]-3,5-di-t-butyl-4-hydroxybenzamide

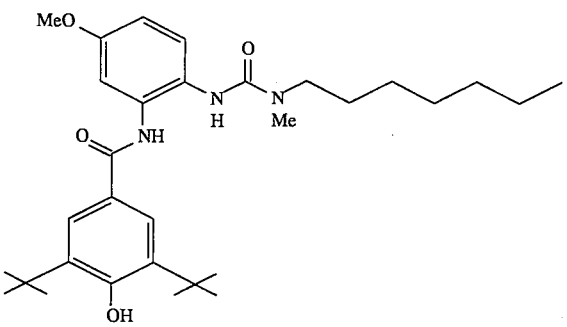

The title compound was prepared by similar procedure as mentioned in Example 17, using N-methylheptylamine instead of cyclopentylamine.

m.p.152°–153° C.

$^1$H-NMR (δ ppm, CDCl$_3$) 9.70(1H, br.s), 7.86(2H, s), 7.29(1H, d, J=3 Hz), 7.06(1H, d, J=9 Hz), 6.84(1H, s), 6.59(1H, dd, J=9 Hz, 3 Hz), 5.61(1H, s), 3.65(3H, s), 3.31(2H, t, J=8 Hz), 2.98(3H, s), 1.50(18H, s), 1.20–1.30(10H, m), 0.86(3H, t, J=7 Hz)

IR(cm$^{-1}$) 3470, 3270, 2880, 2870, 1610, 1520, 1420, 1240

EXAMPLE 22

1-[N-[2-(3,5-di-t-butyl-4-hydroxybenzamido)phenyl]carbamoyl]-4-methylpiperazine

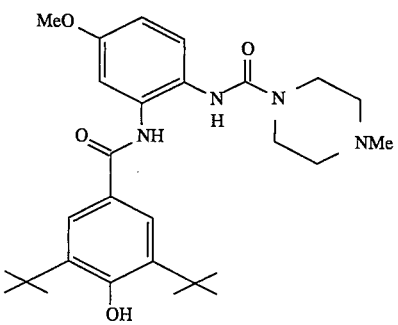

The title compound was prepared by similar procedure as mentioned in Example 17, using N-methylpiperazine instead of cyclopentylamine.

m.p.160°–161° C.

$^1$H-NMR (δ ppm, CDCl$_3$) 9.56(1H, s), 7.84(2H, s), 7.51(1H, s), 7.02–7.05(2H, m), 6.54(1H, dd, J=9 Hz, 3 Hz), 5.63(1H, s), 3.53(4H, t, J=5 Hz), 3.45(3H, s), 2.41(4H, t, J=5 Hz), 2.31(3H, s), 1.51(18H, s)

IR(cm$^{-1}$) 3450, 3250, 2950, 1640, 1600, 1500, 1440, 1300, 1260, 1240, 1090, 1000

Following similar procedure as mentioned in EXAMPLE 1 (4), 1-[N-[2-(3,5-di-t-butyl-4-hydroxybenzamido)phenyl]carbamoyl]-4-methylpiperazine monohydrochloride was obtained as crystals.

m.p.184°–185° C.

EXAMPLE 23

N-[2-[3-(2-pyridylmethyl)ureido]-5-methoxyphenyl]-3,5-di-t-butyl-4-hydroxybenzamide

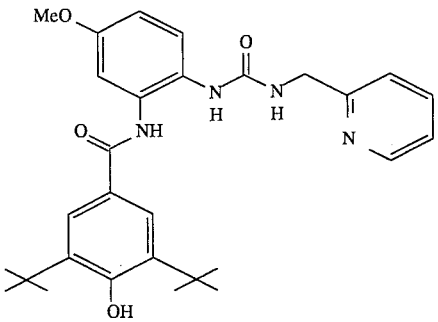

The title compound was prepared by similar procedure as mentioned in Example 17, using 2-(aminomethyl)pyridine instead of cyclopentylamine.

m.p.181°–182 ° C.

$^1$H-NMR (δ ppm, CDCl$_3$) 9.65(1H, s), 8.34(1H, d, J=4 Hz), 7.79(2H, s), 7.63(1H, s ), 7.46 (1H, t, J=7 Hz), 7.26(1H, s), 7.13(1H, d, J=8 Hz), 7.05–7.12(1H, m), 6.88(1H, d, J=9 Hz), 6.56(1H, dd, J=9 Hz, 2 Hz), 6.11(1H, br.s), 5.60(1H, s), 4.49(2H, d, J=5 Hz), 3.75(3H, s), 1.41(18H, s)

IR(cm$^{-1}$) 3400, 2950, 1640, 1600, 1520, 1430, 1320, 1240, 1200, 1110

EXAMPLE 24

N-[2-[3-benzyl-3-(2-pyridylmethyl)ureido]-5-methoxyphenyl]-3,5-di-t-butyl-4-hydroxybenzamide

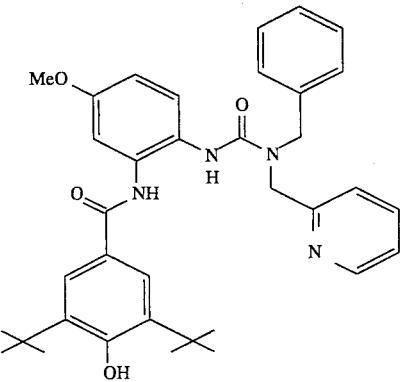

The title compound was prepared by similar procedure as mentioned in Example 17, using 2-(N-benzylaminomethyl)pyridine instead of cyclopentylamine.

m.p.165°–166° C.

$^1$H-NMR (δ ppm, CDCl$_3$) 10.00(1H, br.s), 8.49(1H, d, J=4 Hz), 7.90(2H, s), 7.64(1H, d, J=2 Hz), 7.54–7.58(1H, m), 7.12–7.22(7H, m), 7.03(1H, d, J=9 Hz), 6.89(1H, d, J=8 Hz), 6.69(1H, dd, J=9 Hz, 3 Hz), 5.57(1H, s), 4.66(2H, s), 4.42(2H, s), 3.82(3H, s), 1.44(18H, s)

IR(cm$^{-1}$) 3450, 2950, 1650, 1600, 1530, 1480, 1420, 1260, 1240

Subsequently, following similar procedure as mentioned in Example 1 (4), N-[2-[3-benzyl-3-(2-pyridylmethyl)ureido]-5-methoxyphenyl]-3,5-di-t-butyl-4-hydroxybenzamide monohydrochloride was obtained as crystals.

m.p.142°–144° C.

EXAMPLE 25

N-[2-[3-(3,9-dimethyl-3,9-diazabicyclo[3.3.1]nona-7-yl)-ureido]-5-methoxyphenyl]-3,5-di-t-butyl-4-hydroxybenzamide

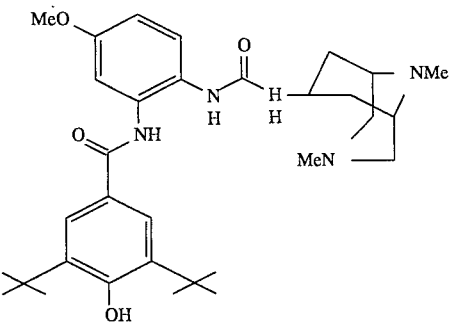

The title compound was prepared by similar procedure as mentioned in Example 17, using 7-amino-3,9-dimethyl-3,9-diazabicyclo[3.3.1]nonane instead of cyclopentylamine.

m.p.210°–211° C.

$^1$H-NMR (δ ppm, CDCl$_3$) 8.84(1H, br.s), 8.10(1H, d, J=2 Hz), 7.75(2H, s), 7.26(1H, s), 7.11(1H, d, J=8 Hz), 6.69(1H, dd, J=8 Hz, 3 Hz), 5.65(1H, s), 5.64(1H, s), 4.25(1H, t, J=7 Hz), 3.84(3H, s), 2.68(2H, br.s), 2.40(3H, s), 2.26–2.35(6H, m), 1.61–1.67(3H, m), 1.48(18H, s), 1.25(2H, d, J=14 Hz)

IR(cm$^{-1}$) 3420, 3250, 2950, 1650, 1530, 1500, 1430, 1260, 1240

Subsequently, following similar procedure as mentioned in Example 1 (4), N-[2-[3-(3,9-dimethyl-3,9-diazabicyclo [3.3.1]nona-7-yl)ureido]-5-methoxyphenyl]-3,5-di-t-butyl-4-hydroxybenzamide dihydrochloride was obtained as crystals.

m.p.265°–270° C.

EXAMPLE 26

N-[2-(3-benzyl-3-cycloheptylureido)-5-methoxyphenyl]-3,5-di-t-butyl-4-hydroxybenzamide

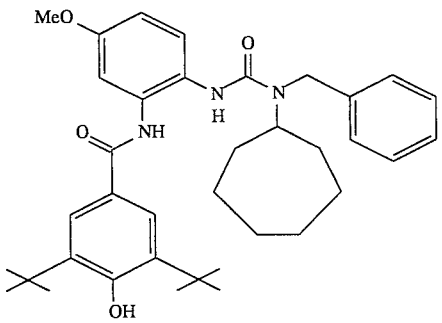

The title compound was prepared by similar procedure as mentioned in Example 17, using N-benzylcycloheptylamine instead of cyclopentylamine.

m.p.125°–130° C.

¹H-NMR (δ ppm, CDCl₃) 9.94 (1H, s ), 7.89 (2H, s ), 7.48(1H, s), 7.33–7.18(5H, m), 6.53–6.41(2H, m), 6.34–6.22(1H, m), 5.60(1H, s ), 4.48(2H, s), 4.48–4.36(1H, m), 3.69(3H, s), 1.95–1.85(2H, m), 1.72–1.50(10H, s), 1.50(18H, s)

IR(cm⁻¹) 3420, 3400, 3280, 2928, 1640, 1602, 1516, 1238, 697

EXAMPLE 27

N-[2-[3-cycloheptyl-3-(2-pyridylmethyl)ureido]-5-methoxyphenyl]-3,5-di-t-butyl-4-hydroxybenzamide

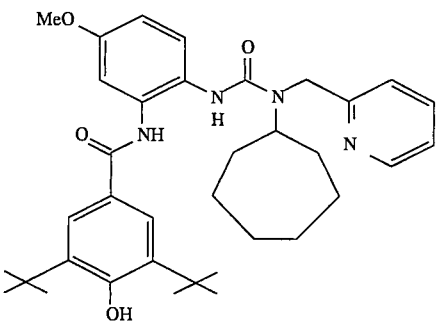

The title compound was prepared by similar procedure as mentioned in Example 17, using 2-(N-cycloheptylaminomethyl)pyridine instead of cyclopentylamine.

m.p.165°–166° C.

¹H-NMR (δ ppm, CDCl₃) 10.12(1H, br.s), 9.63(1H, br), 8.48(1H, d, J=5 Hz), 7.90(2H, s), 7.73–7.65(2H, m), 7.31(1H, d, J=8 Hz), 7.27–7.20(1H, m), 7.01(1H, d, J=9 Hz), 6.65(1H, dd, J=10 Hz, 3 Hz), 5.57(1H, s), 4.45(2H, s), 4.40–4.31(1H, m), 3.82(3H, s), 1.84–1.74(2H, m), 1.73–1.50(10H, m), 1.49(18H, s)

IR(cm⁻¹) 3470, 3240, 2928, 1662, 1635, 1599, 1522, 1469, 1426, 1400, 1304, 1239

EXAMPLE 28

N-[2-[3-(2,4-difluorobenzyl)-3-(2-pyridylmethyl)ureido]-5-methoxyphenyl]-3,5-di-t-butyl-4-hydroxybenzamide

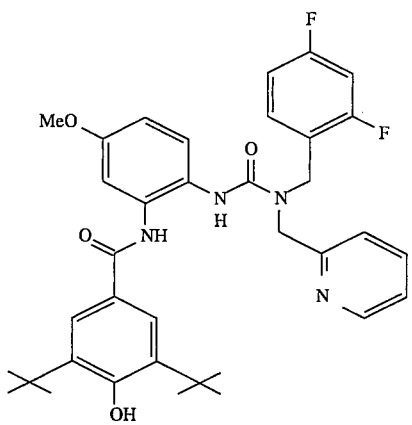

The title compound was prepared by similar procedure as mentioned in Example 17, using 2-[N-(2,4-difluorobenzyl)aminomethyl]pyridine instead of cyclopentylamine.

m.p.176°–178° C.

¹H-NMR (δ ppm, CDCl₃) 9.84(1H, br.s), 9.63(1H, br), 8.46(1H, d, J=4 Hz), 7.86(2H, s), 7.66–7.58(2H, m), 7.28–7.16(2H, m), 7.12–7.06(2H, m), 6.78–6.66(2H, m), 6.53–6.46 (1H, m), 5.58(1H, s), 4.66(2H, s), 4.43(2H, s), 3.82(3H, s), 1.44(18H, s)

IR(cm⁻¹) 3520, 3300, 2958, 1645, 1611, 1545, 1537, 1507, 1484, 1428, 1238, 850

EXAMPLE 29

N-[2-[3-benzyl-3-(3-pyridylmethyl)ureido]-5-methoxyphenyl]-3,5-di-t-butyl-4-hydroxybenzamide

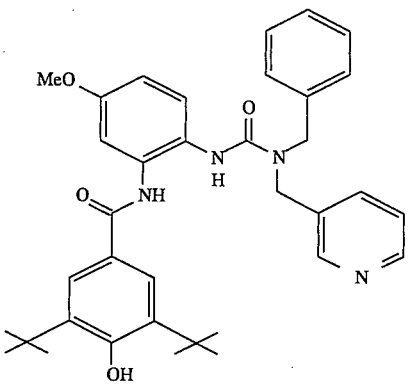

The title compound was prepared by similar procedure as mentioned in Example 17, using 3-(N-benzylaminomethyl)pyridine instead of cyclopentylamine.

m.p.120°–128° C.

¹H-NMR (δ ppm, CDCl₃) 9.64(1H, s), 8.48–8.42(2H, m), 7.81(2H, s), 7.55–7.46(2H, m), 7.26–7.07(7H, m), 6.89(1H, d, J=9 Hz), 6.56(1H, dd, J=9.3 Hz), 5.64 (1H, s), 4.58(2H, s), 4.50(2H, s), 3.55(3H, s), 1.45(18H, s)

IR(cm⁻¹) 3430, 3230, 2960, 1640, 1620, 1524, 1215, 1110, 713, 700

EXAMPLE 30

N-[5-fluoro-2-(3-heptylureido)phenyl]-3,5-di-t-butyl-4-hydroxybenzamide

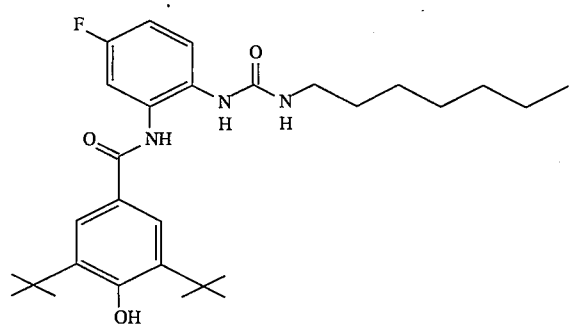

(1) 4-fluoro-2-nitroaniline (1.56 g), heptyl isocyanate (1.41 g) and 4-dimethylaminopyridine (0.37 g) were stirred in toluene (5 ml) at 80°–90 C. for 5 hrs. This solution was diluted with ethyl acetate, washed with 1N hydrochloric acid, sodium hydrogen carbonate solution, water and saturated saline, dried over anhydrous MgSO₄, and the solvent was distilled off. The resulted crystals were washed with hexane to give 1-(4-fluoro-2-nitrophenyl)-3-heptylurea (1.95 g, 66%).

(2) To a suspension of 1-(4-fluoro-2-nitrophenyl)-3-heptylurea (1.49 g) in ethanol (10 ml) was added a catalytic amount of 10% palladium/carbon to perform catalytic reduction at a pressure of 1–2.5 atms at room temperature for 5 hrs. The catalyst was filtered off, and the solvent was distilled off. Crystallization of the residue from hexane gave 1-(2-amino-4-fluorophenyl)-3-heptylurea (1.26 g, 95%).

(3) 1-(2-amino-4-fluorophenyl)-3-cyclopentylurea (1.07 g), 3,5-di-t-butyl-4-hydroxybenzoic acid (1.00 g) and dicyclohexylcarbodiimide (0.99 g) were stirred in dichloromethane (35 ml) at room temperature for 3 hrs. After filtering off the insolubles and distilling off the solvent, the residue was purified by a silica gel column chromatography (chloroform:ethyl acetate=10:1) to yield N-[5-fluoro-2-(3-heptylureido)phenyl]-3,5-di-t-butyl-4-hydroxybenzamide (1.35 g, 68%) as crystals.

m.p.192°–194° C.

$^1$H-NMR (δ ppm, CDCl$_3$) 10.02(1H, br.s), 7.82(2H, s), 7.75(1H, m), 6.98(1H, br.s), 6.65(1H, m), 6.57(1H, m), 5.66(1H, s), 5.21(1H, br.s), 3.12(2H, d, J=6 Hz), 1.50–1.40(2H, m), 1.47(18H, s), 1.30–1.20(8H, m), 0.85(3H, t, J=6 Hz)

IR(cm$^{-1}$) 3628, 3346, 2954, 2928, 1640, 1532, 1430, 1237

EXAMPLE 31

N-[2-(3-adamantylureido)-5-fluorophenyl]-3,5-di-t-butyl-4-hydroxybenzamide

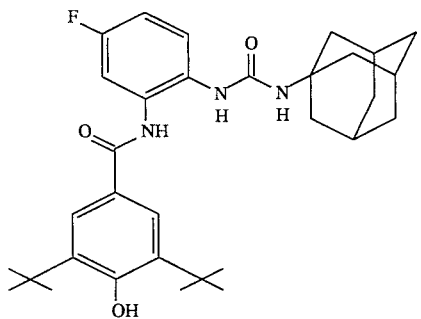

The title compound was prepared by similar procedure as mentioned in Example 30, using 1-adamantyl isocyanate instead of heptyl isocyanate.

m.p.182°–185° C.

$^1$H-NMR (δ ppm, CDCl$_3$) 9.62(1H, br.s), 7.82(2H, s), 7.66(1H, dd, J=10 Hz, 3 Hz), 6.91(1H, dd, J=9 Hz, 6 Hz), 6.88(1H, m), 6.38(1H, br.s), 5.66(1H, s), 4.53(1H, br.s), 2.02(3H, br.s), 1.89(6H, br.s), 1.64(6H, br.s), 1.50(18H, s)

IR(cm$^{-1}$) 3604, 3404, 3262, 2908, 1649, 1615, 1543, 1433, 1238, 756

EXAMPLE 32

N-[5-fluoro-2-(3-heptyl-3-methylureido)phenyl]-3,5-di-t-butyl-4-hydroxybenzamide

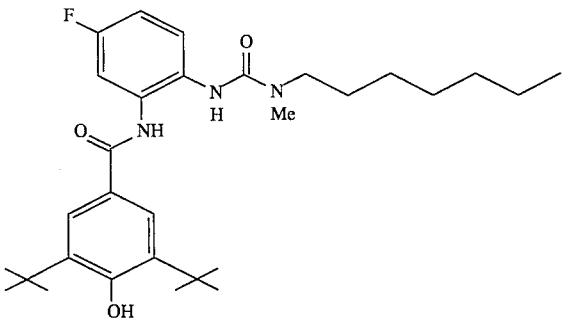

(1) To a solution of 4-fluoro-2-nitroaniline (1.56 g) and diisopropylamine (1.68 ml) in dichloromethane (20 ml) was added dropwise under ice-cooling phenyl chloroformate (1.51 g). After stirring the mixture at room temperature overnight, the reaction solution was washed with water, saturated saline, dried over anhydrous MgSO$_4$ and the solvent was distilled off. Crystallization of the residue from diisopropyl ether afforded phenyl 4-fluoro-2-nitrophenylcarbamate (0.79 g, 29%) as crystals.

(2) Phenyl 4-fluoro-2-nitrophenylcarbamate (0.70 g) and N-methylheptylamine (0.33 g) were dissolved in xylene (5 ml) and the solution was heated under reflux for 2 hrs. The solvent was distilled off and the residue was purified by a silica gel column chromatography (hexane:ethyl acetate= 3:1) to give 1-(4-fluoro-2-nitrophenyl)-3-heptyl-3-methylurea as an oily product.

(3) The oily product was suspended in ethanol (15 ml), a catalytic amount of 10% palladium/carbon was added to perform catalytic reduction at a pressure of 1–2.5 arms at room temperature for 2 hrs. Filtration of the catalyst and distilling off the solvent gave 1-(2-amino-4-fluorophenyl)3-heptyl-3-methylurea (0.82 g, 99%) as an oily product.

(4) A solution of 1-(2-amino-4-fluorophenyl)-3-heptyl-3-methylurea (0.82 g), 1-ethyl-3-(3-dimethylaminopropyl)carbodiimide monohydrochloride (0.67 g) and 3,5-di-t-butyl-4-hydroxybenzoic acid (0.88 g) dissolved in dichloromethane (10 ml) was stirred at room temperature overnight. The reaction solution was washed with water, saturated saline, dried over anhydrous MgSO$_4$, and the solvent was distilled off. Purification of the residue by a silica gel column chromatography gave N-[5-fluoro-2-(3-heptyl-3-methylureido)phenyl]-3,5-di-t-butyl-4-hydroxybenzamide (0.84 g, 56%).

m.p.164°–167° C.

$^1$H-NMR (δ ppm, CDCl$_3$) 9.80(1H, br.s), 7.82(2H, s), 7.30–7.20(2H, m), 7.12(1H, dd, J=9 Hz, 6 Hz), 6.55(1H, m), 5.64(1H, s), 3.32(2H, d, J=7 Hz), 3.00(3H, s), 1.60–1.40(20H, m), 1.35–1.20(8H, m), 0.86(3H, t, J=7 Hz)

IR(cm$^{-1}$) 3424, 3274, 2956, 2924, 2854, 1633, 1609, 1526, 1432, 1315, 1241, 1112

EXAMPLE 33

N-[4,5-dichloro-2-(3-heptylureido)phenyl]-3,5-di-t-butyl-4-5-hydroxybenzamide

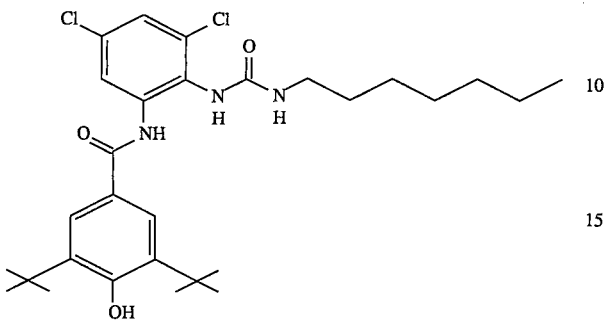

(1) 4,5-dichloro-2-nitroaniline (2.07 g), heptyl isocyanate (1.41 g) and 4-dimethylaminopyridine (0.37 g) were stirred in toluene (5 ml) at 80°–90° C. for 5 hrs. This solution was diluted with ethyl acetate, washed with 1N hydrochloric acid, sodium hydrogen carbonate solution, water and saturated saline, successively, dried over anhydrous $MgSO_4$ and the solvent was distilled off. Purification of the residue by a silica gel column chromatography (hexane:ethyl acetate= 3:1) gave 1-(4,5-dichloro)phenyl-3-heptylurea (2.00 g, 58%) as crystals.

(2) To a suspension of 1-(4,5-dichloro)phenyl-3-heptylurea (1.74 g) in ethanol (10 ml) was added a catalytic amount of 10% palladium/carbon to perform catalytic reduction under a pressure of 1–2.5 atms at room temperature for 5 hrs. After filtering the catalyst and distilling off the solvent, crystallization of the residue from methanol afforded 1-(2-amino-4,5-dichlorophenyl)-3-heptylurea (0.54 g, 34%).

(3) 1-(2-amino-4,5-dichlorophenyl)-3-cyclopentylurea (0.48 g), 3,5-di-t-butyl-4-hydroxybenzoic acid (0.38 g) and dicyclohexylcarbodiimide (0.37 g) were stirred in dichloromethane (35 ml) at room temperature for 3 hrs. After filtering off the insolubles and distilling off the solvent, the residue was purified by a silica gel column chromatography (chloroform:ethyl acetate=20:1) to give N-[4,5-dichloro-2-(3-heptylureido)phenyl]-3,5-di-t-butyl-4-hydroxybenzamide (1.35 g, 68%) as crystals.

m.p. 209°–212° C.

$^1$H-NMR (d ppm, $CDCl_3$) 10.16(1H, br.s), 7.86(2H, s), 7.65(1H, s), 7.52(1H, br.s), 6.85(1H, br.s), 5.69(1H, s), 4.99(1H, br.s), 3.15(2H, q, J=6 Hz), 1.60–1.40(20H, m), 1.40–1.20(8H, m), 0.87(3H, t, J=6 Hz)

IR($cm^{-1}$) 3610, 3425, 3294, 2954, 1662, 1638, 1526, 1235

EXAMPLE 34

N-[2-(3-adamantylureido)-4,5-dichlorophenyl]-3,5-di-t-butyl-4-hydroxybenzamide

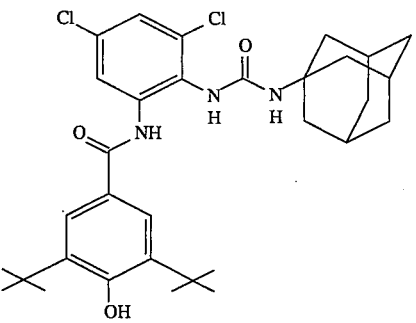

The title compound was prepared by similar procedure as mentioned in Example 33, using 1-adamantyl isocyanate instead of heptyl isocyanate.

m.p.203°–207° C.

$^1$H-NMR (δ ppm, $CDCl_3$) 9.96(1H, br.s), 8.19(1H, s), 7.88(1H, br.s), 7.79(2H, s), 7.57(1H, s), 7.53(1H, s), 6.69(1H, br.s), 2.01(3H,br.s), 1.92(6H, br.s), 1.62(6H, br.s), 1.43(18H, s)

IR($cm^{-1}$) 3618, 3320, 2916, 2850, 1640, 1631, 1575, 1313, 1244, 1233

EXAMPLE 35

N-[4,5-dichloro-2-(3-heptyl-3-methylureido)phenyl]-3,5-di-t-butyl-4-hydroxybenzamide

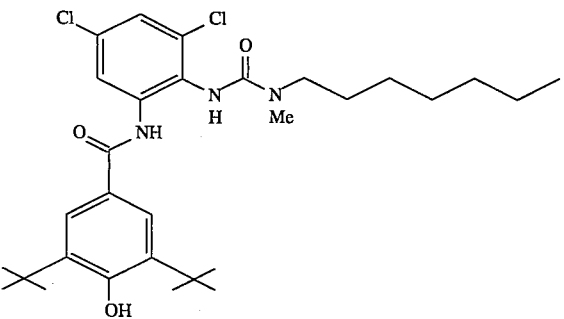

The title compound was prepared by similar procedure as mentioned in Example 32, using 4,5-dichloro-2-nitroaniline instead of 4-fluoro-2-nitroaniline.

m.p.187°–190° C.

$^1$H-NMR (δ ppm, $CDCl_3$) 9.97(1H, br.s), 8.07(1H, br.s), 7.88(2H, s), 7.39(1H, s), 7.27(1H, s), 5.65(1H, s) 3.34 (2H, m), 3.03(3H, s), 1.60–1.50(20H, m), 1.40–1.20(8H, m), 0.87(3H, t, J=6 Hz)

IR($cm^{-1}$) 3500, 2954, 2928, 1634, 1590, 1526, 1493, 1427, 1320, 1234, 1116

EXAMPLE 36

N-[2-(3-heptylureido)-4-methoxyphenyl]-3,5-di-t-butyl-4-hydroxybenzamide

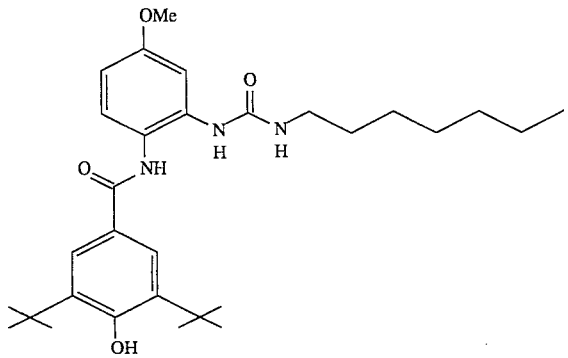

(1) 4-methoxy-2-nitroaniline (1.68 g), 3,5-di-t-butyl-4-hydroxybenzoic acid (2.50 g) and dicyclohexylcarbodiimide (2.06 g) were stirred in dichloromethane (12 ml) at room temperature for 6 days. After filtering off the insolubles and distilling off the solvent, the residue was purified by a silica gel column chromatography (hexane:ethyl acetate=20:1) and crystallized from hexane-ethyl acetate to give N-(4-methoxy-2-nitrophenyl-3,5-di-t-butyl-4-hydroxybenzamide (1.56 g, 39%).

(2) To a solution of N-(4-methoxy-2-nitrophenyl)-3,5-di-t-butyl-4-hydroxybenzamide (1.50 g) in ethanol (10 ml) was added a catalytic amount of 10% palladium/carbon to perform catalytic reduction under a pressure of 1–2.5 arms at room temperature for 5 hrs. After filtering the catalyst and distilling off the solvent, crystallization of the residue from hexane-ethyl acetate afforded N-(2-amino-4-methoxyphenyl)-3,5-di-t-butyl-4-hydroxybenzamide (0.79 g, 57%).

(3) n-caprylic acid (0.32 g), diphenylphosphoryl azide (0.53 ml) and triethylamine (0.34 ml) were stirred in toluene (5 ml) at room temperature for 3 hrs. and additionally for 2 hrs. at 80°–90° C. To the mixture was added under ice-cooling N-(2-amino-4-methoxyphenyl)-3,5-di-t-butyl-4-hydroxybenzamide (0.44 g), and the mixture was stirred overnight while returning slowly to room temperature. The solvent was distilled off and the residue was purified by a silica gel column chromatography (chloroform) to give N-[2-(3-heptylureido)-4-methoxyphenyl]-3,5-di-t-butyl-4-hydroxybenzamide (0.57 g, 93%) as a non-crystallizable solid.

$^1$H-NMR (δ ppm, CDCl$_3$) 10.02(1H, s), 7.88(2H, s), 7.39(1H, d, J=9 Hz), 7.31(1H, s), 6.61(1H, dd, J=9 Hz, 3 Hz), 6.01(1H, s), 5.64(1H, s), 5.17(1H, br.s), 3.36(3H, s), 3.03(2H, td, J=6 Hz, 8 Hz), 1.48(18H, s), 1.40–1.20(10H, m), 0.87(3H, t, J=7 Hz)

IR(cm$^{-1}$) 3630, 3300, 1632, 1516, 1432, 1237

EXAMPLE 37

2-(3-heptylureido)phenyl 3,5-di-t-butyl-4-hydroxybenzoate

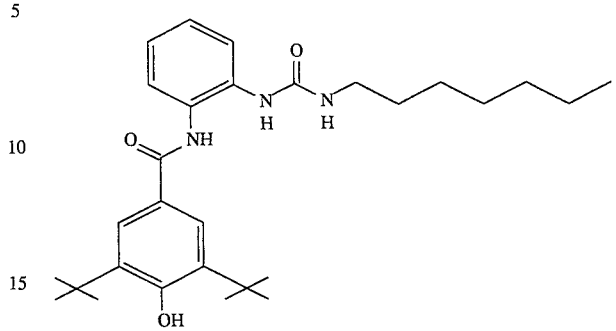

(1) A mixture of n-caprylic acid (1.44 g), diphenylphosphoryl azide (2.80 ml) and triethylamine (2.09 ml) was stirred in toluene (10 ml) at room temperature for 3 hrs. and additionally for 2 hrs. at 80°–90° C. To the ice-cooled mixture was added o-aminophenyl (1.09 g) and the mixture was stirred overnight while returning slowly to room temperature. The solvent was distilled off and the residue was purified by a silica gel column chromatography (hexane:ethyl acetate=2:1) to give 1-(2-hydroxyphenyl)-3-heptylurea (1.58 g, 63%) as crystals. The crystals (0.50 g), 3,5-di-t-butyl-4-hydroxybenzoic acid (0.50 g) and dicyclohexylcarbodiimide (0.42 g) were stirred in dichloromethane (5 ml) at room temperature overnight. After filtering off the insolubles and distilling off the solvent, the residue was purified by a silica gel column chromatography (chloroform:ethyl acetate=10:1) to give 2-(3-heptyl)ureidophenyl 3,5-di-t-butyl-4-hydroxybenzoate (0.58 g, 60%) as crystals.

m.p.160°–162° C.

$^1$H-NMR (δ ppm, CDCl$_3$) 8.04(2H, m), 7.77(1H, d, J=8 Hz), 7.26(1H, m), 7.17(2H, m), 6.12(1H, br.s), 5.84(1H, s), 4.64(1H, br.t), 3.16(2H, q-like, J=7 Hz), 1.60–1.40(20H, m), 1.40–1.20(8H, m), 0.86(3H, t, J=7 Hz)

IR(cm$^{-1}$) 3312, 2958, 2928, 1736, 1720, 1645, 1600, 1552, 1305, 1223, 1178, 1101

EXAMPLE 38

2-(3-heptylureido)phenyl 3,5-di-t-butyl-4-[(N-heptyl)carbamoyloxy]benzoate

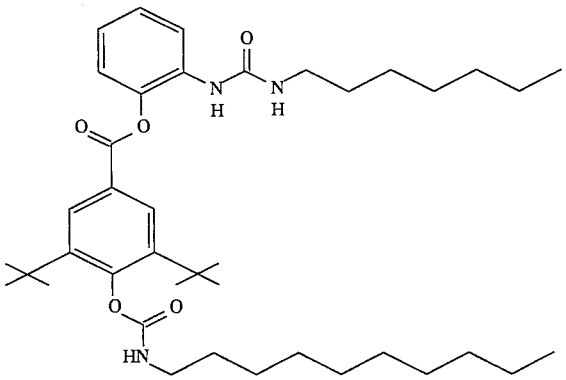

A mixture of o-nitrophenol (1.39 g), 3,5-di-t-butyl-4-hydroxybenzoic acid (2.50 g) and trifluoroacetic anhydride (8.5 ml) was stirred at room temperature overnight. The mixture was poured into ice water, neutralized with sodium hydrogen carbonate, extracted with ethyl acetate, washed with water, saturated saline, and dried over anhydrous MgSO$_4$. The solvent was distilled off and crystallization of the residue from diisopropyl ether afforded 2-nitrophenyl 3,5-di-t-butyl-4-hydroxybenzoate (2.60 g, 70%).

To a solution of the crystals (1.11 g) in ethanol (10 ml) was added a catalytic amount of 5% palladium/carbon to perform catalytic reduction under 1–2.5 arms at room temperature for 5 hrs. After filtration of the catalyst, the solvent was distilled off to give 2-aminophenyl 3,5-di-t-butyl-4-hydroxybenzoate (0.86 g, 84%) as crystals.

A mixture of n-caprylic acid (0.32 diphenylphosphoryl azide (0.53 ml) and triethylamine (0.34 ml) was stirred in toluene (5 ml) at room temperature for 3 hrs. and additionally for 2 hrs. at 80°–90° C. To the ice-cooled mixture was added 2-aminophenyl 3,5-di-t-butyl-4-hydroxybenzoate (0.51 g) and the mixture was stirred overnight while returning slowly to room temperature. The solvent was distilled off and the residue was purified by a silica gel column chromatography to give 2-(3-heptylureido)phenyl 3,5-di-t-butyl-4-[(N-heptyl)carbamoyloxy]benzoate (0.18 g, 19%) as a non-crystallizable solid.

$^1$H-NMR (δ ppm, CDCl$_3$) 7.80–7.78(3H, m), 7.24(1H, d, J=7 Hz), 7.19–7.10(3H, m), 5.26(1H, br.t), 5.18(1H, br.t), 3.31–3.21(4H, m), 1.50–1.20(38H, m), 0.90–0.80(6H, m)

IR(cm$^{-1}$) 3314, 2960, 2930, 1721, 1525, 1198, 1117, 749

EXAMPLE 39

N-[2-(3-heptylureido)-3-pyridyl]-3,5-di-t-butyl-4-hydroxybenzamide

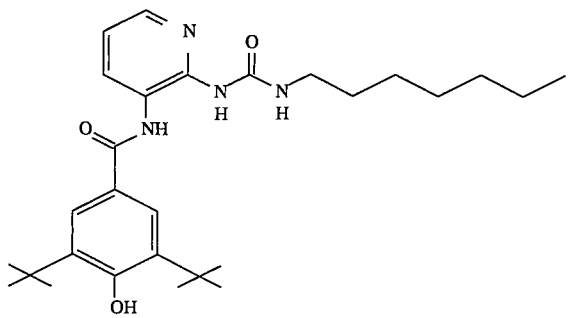

(1) A mixture of 2-amino-3-nitropyridine (1.39 g), heptyl isocyanate (1.41 g) and 4-dimethylaminopyridine (0.37 g) was stirred in toluene (5 ml) at 100°–110° C. for 5 hrs. The solvent was distilled off and the residue was purified by a silica gel column chromatography (hexane:ethyl acetate= 2:1) to give 1-(3-nitro-2-pyridyl)-3-heptylurea (1.03 g, 37%) as crystals.

(2) To a suspension of 1-(3-nitro-2-pyridyl)-3-heptylurea (1.00 g) in ethanol (10 ml) was added a catalytic amount of 10% palladium/carbon to perform catalytic reduction under 1–2.5 atms at room temperature for 5 hrs. After filtering the catalyst and distilling off the solvent, the crystallization of the residue from hexane afforded 1-(3-amino-2-pyridyl)-3-heptylurea (0.89 g, 99%).

(3) A mixture of 1-(3-amino-2-pyridyl)-3-heptylurea (0.80 g), 3,5-di-t-butyl-4-hydroxybenzoic acid (0.80 g) and 1-ethyl-3-(3-dimethylaminopropyl)carbodiimide monohydrochloride (0.67 g) was stirred in dichloromethane (35 ml) at room temperature for 3 hrs. After filtering off the insolubles and distilling off the solvent, the residue was purified by a silica gel column chromatography (chloroform:methanol=30:1) to give N-[2-(3-heptylureido)-3-pyridyl]-3,5-di-t-butyl-4-hydroxybenzamide (1.34 g, 87%) as a non-crystallizable solid.

$^1$H-NMR (δ ppm, CDCl$_3$) 9.58(1H, br.s), 9.48(1H, br.s), 9.06(1H, br.s), 8.34(1H, dd, J=8 Hz, 1 Hz), 7.96(1H, dd, J=5 Hz, 1 Hz ), 7.87(2H, s), 6.97(1H, dd, J=8 Hz, 5 Hz), 5.59(1H, s), 2.86(2H, q, J=6 Hz ), 1.44 (18H, s), 1.40–1.10(10H, m), 0.85(3H, t, J=6 Hz)

IR(cm$^{-1}$) 3622, 3250, 2956, 2926, 1679, 1564, 1424, 1311, 1236, 1114

EXAMPLE 40

N-[2-(3-adamantylureido)-3-pyridyl]-3,5-di-t-butyl-4-hydroxybenzamide

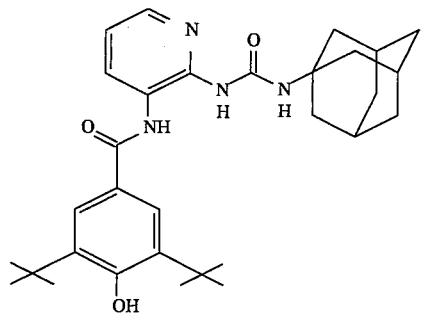

The title compound was prepared by similar procedure as mentioned in Example 39, using 1-adamantyl isocyanate instead of heptyl isocyanate.

m.p.198°–202° C. $^1$H-NMR (δ ppm, CDCl$_3$) 9.55(1H, br.s), 9.24(1H, br.s), 8.38(1H, br.s), 8.25(1H, dd, J=6 Hz, 2 Hz), 7.97(1H, dd, J=5 Hz, 2 Hz), 7.89(2H, s), 6.96(1H, dd, J=6 Hz, 5 Hz), 5.58(1H, s), 1.90–1.70(9H, m), 1.60–1.40(24H, m)

IR(cm$^{-1}$) 3732, 3266, 2908, 1681, 1562, 1455, 1319, 1237

EXAMPLE 41

N-[3-(3-heptylureido)-4-pyridyl]-3,5-di-t-butyl-4-hydroxybenzamide

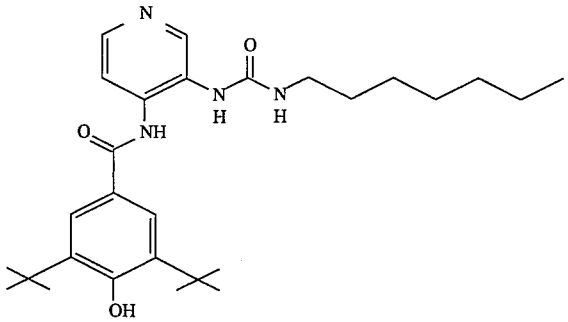

(1) A mixture of 3,4-diaminopyridine (1.09 g), heptyl isocyanate (1.41 g) and 4-dimethylaminopyridine (0.37 g) was stirred in toluene (10 ml) at 50°–60° C. for 5 hrs. The solvent was distilled off and the residue was purified by a silica gel column chromatography (chloroform:methanol=

4:1) to give 1-(4-amino-3-pyridyl)-3-heptylurea (1.09 g, 37%) and crystals.

(2) A mixture of 1-(4-amino-3-pyridyl)-3-heptylurea (0.50 g), 3,5-di-t-butyl-4-hydroxybenzoic acid (0.60 g) and 1-ethyl-3-(3-dimethylaminopropyl)carbodiimide monohydrochloride (0.46 g) was stirred in dichloromethane (10 ml) at room temperature overnight. The reaction solution was washed with water, saturated saline and dried over anhydrous $MgSO_4$. The solvent was distilled off and the residue was purified by a silica gel column chromatography (chloroform:methanol=20:1) to give N-[3-(3-heptylureido)-4-pyridyl]-3,5-di-t-butyl-4-hydroxybenzamide (0.15 g, 16%) as crystals.

m.p.177°–180° C.

$^1$H-NMR (δ ppm, $CDCl_3$) 10.58(1H, br.s), 8.25(1H, d, J=5 Hz), 8.01(2H, m), 7.89(2H, s), 7.56(1H, br.s), 5.69(1H, s), 5.52(1H, br.s), 3.23(2H, q-like, J=4 Hz), 1.81(2H, m), 1.49(18H, s), 1.39–1.21(8H, m), 1.39–1.21(3H, t, J=7 Hz)

IR($cm^{-1}$) 3360, 2954, 2928, 1646, 1590, 1510, 1434, 1317, 1237, 1113

EXAMPLE 42

N-[2-[3-(1-benzyl-4-piperidyl)ureido]-5-methoxyphenyl]-3,5-di-t-butyl-4-hydroxybenzamide

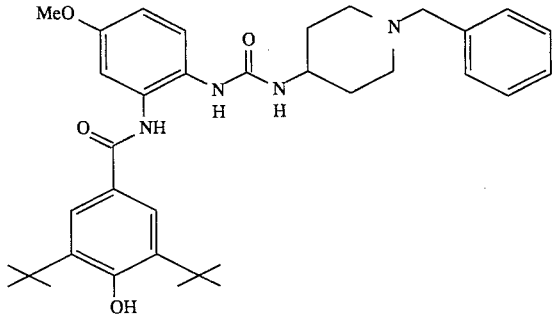

The title compound was prepared by similar procedure as mentioned in Example 17, using 4-amino-1-benzylpiperazine instead of cyclopentylamine m.p.176°–179° C.

$^1$H-NMR (δ ppm, $CDCl_3$) 9.96(1H, br.s),7.82(2H, s), 7.43(1H, br.s), 7.33–7.06(6H, m), 6.64(1H, d, J=8 Hz ), 6.45(1H, dd, J=9, 3 Hz), 5.62(1H, s), 5.17(1H, br.d, J=7 Hz), 3.67(3H, s), 3.62–3.50(1H, m), 3.43(2H, s), 2.78–2.68(2H, m), 2.04–1.94(2H, m), 1.78–1.68(2H, m), 1.44(18H, s), 1.34–1.20(2H, m)

IR($cm^{-1}$) 3400, 2950, 1640, 1525, 1510, 1430, 1235, 740, 700

EXAMPLE 43

1-(1-benzyl-4-piperidyl)-3-[2-[3-(3,5-di-t-butyl-4-hydroxyphenyl)propoxy]phenyl]urea

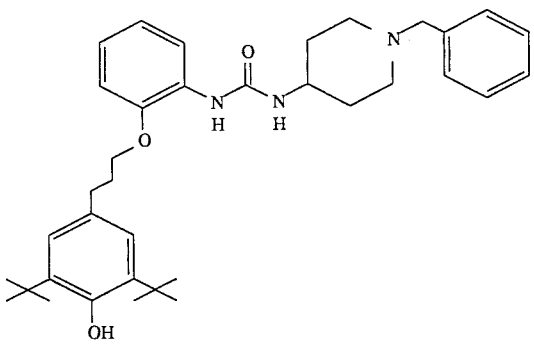

(1) A mixture of 4-(3-bromopropyl)-2,6-di-t-butylphenol (1.20 g), 2-nitrophenol (0.51 g), potassium carbonate (1.01 g) and a catalytic amount of sodium iodide was stirred in dimethylformamide (10 ml) at 60°–70° C. for 1.5 hrs. The reaction solution was poured into water, extracted with ethyl acetate, washed with water and then saturated saline, and dried over anhydrous $MgSO_4$. After distilling off the solvent, the residue was purified by a silica gel column chromatography (hexane:ethyl acetate=10:1) to give 4-[3-(2-nitrophenoxy)propyl]-2,6-di-t-butylphenol (1.05 g, 74%).

(2) To a suspension of 4-[3-(2-nitrophenoxy)propyl]-2,6-di-t-butylphenol (1.03 g) in ethanol (30 ml) was added a catalytic amount of 10% palladium/carbon to carry out catalytic reduction under 3–4 arms at 40° C. for 10 hrs. After filtering off the catalyst, the solvent was distilled off to give 4-[3-(2-aminophenoxy)propyl]-2,6-di-t-butylphenol. This compound was dissolved in dichloromethane (20 ml), to which diisopropylamine (0.75 ml) was added. Phenyl chloroformate (0.84 g) was added dropwise under ice-cooling. After stirring the mixture at room temperature overnight, the reaction solution was washed with water and then saturated saline and dried over anhydrous $MgSO_4$. After distilling off the solvent, the residue was purified by a silica gel column chromatography (hexane:ethyl acetate=15:1) to give 1-(1-benzyl-4-piperidyl)-3-[2-[3-(3,5-di-t-butyl-4-hydroxyphenyl)propoxy]phenyl]urea (1.23 g, 97%).

m.p.148°–149° C.

$^1$H-NMR (δ ppm, $CDCl_3$) 7.95(1H, dd, J=7, 2 Hz), 7.35–7.20(5H, m), 6.97(2H, s), 6.96–6.90(2H, m), 6.81(1H, dd, J=7, 2 Hz), 6.70(1H, s), 5.07(1H, s), 4.56(1H, d, J=8 Hz), 4.03(2H, t, J=7 Hz), 3.62–3.70(1H, m), 3.48(2H, s), 2.81(2H, br.d, J=12 Hz), 2.70(2H, t, J=8 Hz), 2.15–2.09(4H, m), 1.97(2H, br.d, J=11 Hz), 1.42(18H, s), 1.50–1.35(2H, m)

IR($cm^{-1}$) 3636, 3310, 1641, 1549, 1451, 1235, 742

Pharmacological Test

1. ACAT inhibitory activity

The enzyme preparation, ACAT was prepared from liver microsome fractions of male rabbits according to the method of E. E. Largis et al. (Journal of Lipid Research, Vol. 30, pages 681–690, 1989). The activity was calculated by assaying the amount of the labelled cholesteryl esters formed from [1-$^{14}$C]oleoyl-CoA and endogenous cholesterol according to the method of Kazuichi NATORI et al. (Japan J. Pharmacol., Vol. 42, pages 517–523, 1986).

The result is shown in Table 1, in which percent inhibition of the formation of the labelled cholesteryl esters with a compound added at $10^{-7}$M is indicated as index for the ACAT inhibitory activity.

The data reveals that the compounds of the invention have a superior ACAT inhibitory activity. 2. Antioxidative activity Human LDL was incubated in the presence of cupric sulfate ($5 \times 10^{-6}$M) and in the presence or absence of a compound ($10^{-5}$M) for 5 hrs. After the incubation, the peroxidation of low-density lipoproteins (LDL) is evaluated by the formation of malondialdehyde (MDA), which is a sort of lipid peroxides according to the method of Simon J. T. Mao et al. (J. Med. Chem., Vol. 34, pages 298–302, 1991). Activity of the compound is shown by percent inhibition of the MDA formation as compared with control. The result is shown in Table 1. The data indicates that the compounds of the invention significantly lower the formation of the lipid peroxide (MDA).

TABLE 1

| Compounds of Example | ACAT Inhibition (%) | Antioxidant Activity (%) |
|---|---|---|
| 6* | 79 | 82 |
| 7 | 86 | 75 |
| 8 | 85 | 83 |
| 11 | 73 | |
| 12 | 79 | |
| 13 | 88 | |
| 14 | 81 | 96 |
| 19 | 78 | |
| 20 | 99 | |
| 21 | 93 | |
| 30 | 78 | 79 |
| 31 | 91 | |
| 32 | 95 | |
| 35 | 71 | |
| 36 | 77 | 92 |

6*: N-[2-(3-heptylureido)phenyl]-3,5-di-t-butyl-4-hydroxybenzamide

The pharmaceutical preparations comprising the compounds of the invention are prepared by conventional method in accordance with the following formulations.

| Tablets (per tablet) | |
|---|---|
| Compound of Example 8 | 50 mg |
| Hydroxypropylcellulose | 2 mg |
| Corn starch | 10 mg |
| Lactose | 100 mg |
| Magnesium stearate | 3 mg |
| Talc | 3 mg |
| Capsules (per capsule) | |
| Compound of Example 14 | 200 mg |
| Starch | 8 mg |
| Microcrystalline cellulose | 23 mg |
| Talc | 8 mg |
| Magnesium stearate | 5 mg |
| Granules (per divided packet) | |
| Compound of Example 36 | 1 mg |
| Lactose | 99 mg |
| Corn starch | 50 mg |
| Crystalline cellulose | 50 mg |
| Hydroxypropylcellulose | 10 mg |
| Ethanol | 9 mg |

What is claimed is:

1. A compound of formula (1) or a pharmaceutically acceptable salt thereof

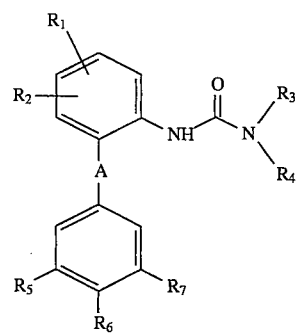

in which:

$R_1$ and $R_2$, which may be the same or different, each represents
a hydrogen atom,
a halogen atom,
a ($C_1$–$C_6$) alkoxy group, $R_3$ and $R_4$, which may be the same or different, each represents
a hydrogen atom,
a ($C_1$–$C_8$) alkyl group,
a cyclo($C_3$–$C_8$) alkyl group,
an aryl($C_1$–$C_6$) alkyl group,
in which the aryl moiety is optionally substituted by one or two substituents selected from the group consisting of halogen, ($C_1$–$C_6$) alkyl and ($C_1$–$C_6$) alkoxy,
a diaryl($C_1$–$C_6$) alkyl group,
a pyridyl($C_1$–$C_6$) alkyl group,
an adamantyl group or
a piperidyl group optionally substituted by aryl($C_1$–$C_6$) alkyl, $R_5$ and $R_7$, which may be the same or different, each represents a hydrogen atom or a ($C_1$–$C_6$) alkyl group, $R_6$ represents —$OR_8$ or —$N(R_8)_2$ wherein $R_8$ represents a hydrogen atom or a ($C_1$–$C_6$) alkyl group, or —$C(O)NHR_3$ wherein $R_3$ is as defined above, $R_6$ and $R_7$ together may form —O—$CH_2$—O— which may be fused with a phenyl ring, A represents

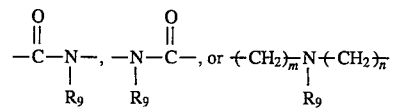

wherein $R_9$ represents a hydrogen atom, a ($C_1$–$C_6$) alkyl group, a ($C_1$–$C_6$) alkylcarbonyl group, a geranyl group or —$C(O)NHR_3$, and m is 0 when n is 1 or m is 1 when n is 0 the alkyl and alkoxy groups or moieties represented by $R_1$ to $R_9$ may be straight or branched with the proviso that when A is

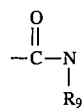

and $R_6$ is $OR_8$, $R_8$ is not a ($C_1$–$C_6$)alkyl group.

2. A compound of claim 1, wherein $R_3$ and $R_4$, which may be the same or different, each represents
a hydrogen atom,
a ($C_5$–$C_7$) cycloalkyl group,
a benzyl group in which the phenyl moiety is optionally substituted by one or two halogen atoms, a diphenyl($C_1$–$C_4$) alkyl group,
a pyridyl($C_1$–$C_4$) alkyl group,
an adamantyl group or
a benzylpiperidyl group,
A represents

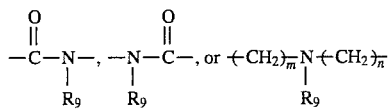

wherein $R_9$ represents a hydrogen atom, a ($C_1$–$C_6$) alkyl group, an acetyl group, a geranyl group or —C(O)$NHR_3$, and when m is 1, n is 0 and when n is 1, m is 0 and alkoxy groups or moieties represented by $R_1$ to $R_9$ may be straight or branched.

3. A compound of claim 2 wherein A represents —C(O)N($R_9$)— or —N($R_9$)C(O)—.

4. A compound of claim 2 wherein A represents —$(CH_2)_m$N($R_9$)$(CH_2)_n$—.

5. A pharmaceutical composition comprising as an active ingredient a pharmaceutically effective amount of a compound of claim 1 or a pharmaceutically acceptable salt thereof and a pharmaceutically acceptable carrier and/or excipient.

6. A pharmaceutical composition of claim 5 for use in the prophylaxis and treatment of hypercholesterolemia and atherosclerosis.

7. N-[2-(3-(2,2-diphenylethyl)ureido]phenyl]-3,5-di-t-butyl-4-hydroxybenzamide, a compound of the formula

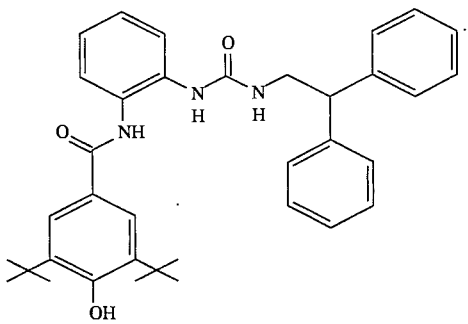

* * * * *

UNITED STATES PATENT AND TRADEMARK OFFICE
CERTIFICATE OF CORRECTION

PATENT NO. : 5,576,335
DATED : NOVEMBER 19, 1996
INVENTOR(S) : SUEDA, ET AL

It is certified that error appears in the above-indentified patent and that said Letters Patent is hereby corrected as shown below:

On the title page, item [75]: Inventors, "Koichi Katasuyama" should read -- Koichi Katsuyama--

Claim 1, lines 55-60 amend

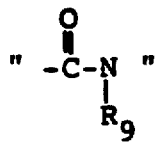

to read

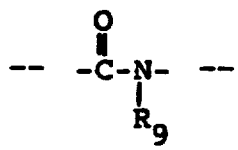

Signed and Sealed this

Eighteenth Day of February, 1997

Attest:

BRUCE LEHMAN

*Attesting Officer*    *Commissioner of Patents and Trademarks*